(12) United States Patent
Kaminuma et al.

(10) Patent No.: US 8,937,090 B2
(45) Date of Patent: Jan. 20, 2015

(54) PARAKERATOSIS INHIBITOR, PORE-SHRINKING AGENT AND EXTERNAL COMPOSITION FOR SKIN

(75) Inventors: Mikiko Kaminuma, Yokohama (JP); Masaru Suetsugu, Yokohama (JP); Toshii Iida, Yokohama (JP); Shinji Inomata, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 2203 days.

(21) Appl. No.: 11/920,053

(22) PCT Filed: Apr. 28, 2006

(86) PCT No.: PCT/JP2006/308984
§ 371 (c)(1),
(2), (4) Date: Apr. 20, 2012

(87) PCT Pub. No.: WO2006/120941
PCT Pub. Date: Nov. 16, 2006

(65) Prior Publication Data
US 2012/0232111 A1 Sep. 13, 2012

(30) Foreign Application Priority Data
May 9, 2005 (JP) ................................. 2005-135630

(51) Int. Cl.
*A61K 31/44* (2006.01)
*A61K 31/135* (2006.01)
*A61K 31/13* (2006.01)
*A61Q 19/00* (2006.01)
*A61K 8/02* (2006.01)
*A61K 8/44* (2006.01)
*A61K 8/49* (2006.01)
*A61K 31/136* (2006.01)
*A61K 31/137* (2006.01)
*A61K 31/131* (2006.01)
*A61Q 1/02* (2006.01)
*A61Q 1/12* (2006.01)

(52) U.S. Cl.
CPC .............. *A61Q 19/00* (2013.01); *A61K 31/136* (2013.01); *A61K 31/137* (2013.01); *A61K 31/131* (2013.01); *A61K 8/0212* (2013.01); *A61K 8/44* (2013.01); *A61K 8/445* (2013.01); *A61K 8/447* (2013.01); *A61K 8/4926* (2013.01); *A61Q 1/02* (2013.01); *A61Q 1/12* (2013.01)
USPC ............................. 514/352; 514/646; 514/667

(58) Field of Classification Search
CPC ....... A61Q 19/00; A61Q 1/12; A61K 8/0212; A61K 8/44; A61K 8/445; A61K 8/447; A61K 8/4926; A61K 31/131; A61K 31/136; A61K 31/137
USPC .......................................... 514/352, 646, 667
See application file for complete search history.

(56) References Cited

U.S. PATENT DOCUMENTS

| 4,016,287 | A | 4/1977 | Eberhardt et al. |
| 2003/0175803 | A1 | 9/2003 | Tsionsky et al. |
| 2004/0220264 | A1 | 11/2004 | Yu et al. |

FOREIGN PATENT DOCUMENTS

| DE | 101 33 197 | 1/2003 |
| JP | 49-85244 | 8/1974 |
| JP | 5-97627 | 4/1993 |
| JP | 5-105619 | 4/1993 |
| JP | 8-99862 | 4/1996 |
| JP | 11-255632 | 9/1999 |
| JP | 2002-241260 | 8/2002 |
| JP | 2003-342195 | 12/2003 |
| WO | 00/40217 A1 | 7/2000 |
| WO | WO 00/40217 | 7/2000 |
| WO | WO 2004/064866 | 8/2004 |

OTHER PUBLICATIONS

European Office Action mailed on Aug. 2, 2013.
Yazawa et al., "Reduction Effect of Pores by Pre Vitamin C Cream and Glycolic Acid", *Fragrance Journal*, 2002, pp. 54-58, vol. 30, No. 2.
Iida et al., Program and Minutes of the 102nd Japanese Dermatological Association Convention, *The Japanese Journal of Dermatology*, 2003, p. 846, vol. 113, No. 5.

*Primary Examiner* — San-Ming Hui
(74) *Attorney, Agent, or Firm* — Amin, Turocy & Watson, LLP

(57) ABSTRACT

The invention provides a parakeratosis inhibitor, pore-shrinking agent, or rough skin preventing/ameliorating agent that has a function such as parakeratosis inhibition, pore shrinkage, or rough skin-inhibition/abatement, poses no safety problems such as sensory irritation, and is very safe, and further provides an external composition for skin to which a compound having the above-mentioned function has been added. The parakeratosis inhibitor, pore-shrinking agent, or rough skin preventing/ameliorating agent comprises one or more compounds selected from the group consisting of β-alanine derivatives and salts thereof. The external composition for skin comprises the one or more compounds selected from the group consisting of β-alanine derivatives and salts thereof as the above-mentioned parakeratosis inhibitor, pore-shrinking agent, or rough skin preventing/ameliorating agent.

7 Claims, No Drawings

PARAKERATOSIS INHIBITOR, PORE-SHRINKING AGENT AND EXTERNAL COMPOSITION FOR SKIN

TECHNICAL FIELD

The present invention relates to a parakeratosis inhibitor for inhibiting parakeratosis caused by sebum; a pore-shrinking agent for inhibiting parakeratosis caused by the irritating components in the sebum around the pore, maintaining normal skin conditions around the pore, and suppressing a conical structure of the pore from becoming conspicuous; a rough skin preventing/ameliorating agent with which rough skin caused by unsaturated fatty acids is prevented/abated; and an external composition for skin having a function such as inhibiting parakeratosis, shrinking pores, or preventing and ameliorating rough skin.

BACKGROUND ART

Today young women in particular are very concerned with conspicuous pores, and an external composition for skin that provides relief for this condition is necessary. However, the mechanism by which pores become conspicuous has not been elucidated, and conventional treatment has been through the use of an astringent cosmetics toner or the removal of keratin plug. Alternatively, a foundation is often used in order to improve appearance. However, the purpose of an astringent cosmetics toner is to tighten the skin, to temporarily reduce the skin surface temperature by an alcohol, or to coagulate the proteins by an organic acid and the like. Consequently, the skin is temporarily tightened, and the results have therefore been unsatisfactory in that there is an increase in stress applied to the skin without a fundamental solution to conspicuous pores.

On the other hand, it has been reported that the derivatives of glycolic acid and ascorbic acid has the effect of pore-shrinking effect (see Non-patent document 1), there are still many unknowns, such as the mechanism of action, the extent of the effect, and the like.

Keratin plug removal is the physical way of a keratin plug, which is clogging the pore. For example, it is known as conventional methods, keratin plug removal agents containing polymer, e.g., keratin plug removal agents containing polymer compounds having salt-generating groups (for example, see Patent Document 1); cosmetics containing water-insoluble cyclodextrin polymers (for example, see Patent Document 2); and cosmetics for keratin plug removal containing 50 mass % or greater of an oil component having a viscosity of 5 to 80 mPa·s/25° C. (for example, see Patent Document 3). The physical force of such methods for keratin plug removal can damage the skin, and side effects on the skin has been a serious problem. The effect of this method is not always satisfactory since the effect thereof is temporary and keratin plug is readily regenerated, and removal of keratin plug may only expand the pore.

The inventors performed considerable research on the mechanism of conspicuous pores in order to develop an external composition for skin that ameliorates conspicuous pores, and discovered such features, among others, as those listed herein below and presented the same at the 102$^{nd}$ Convention of the Japanese Dermatological Association (see Non-Patent Document 2).

(1) the conical depression surrounding a follicle is recognized as a pore, and when this portion is enlarged, the pore becomes conspicuous (2) the stratum corneum of this conical area is in a state of parakeratosis (nuclei that should have disappeared still remain);

(3) people having conspicuous pores also have a large amount of sebum, particularly unsaturated fatty acids;

(4) these unsaturated fatty acids are the cause of parakeratosis;

(5) it is highly probable that the unsaturated fatty acids in sebum are the cause of conspicuous pores, and the like.

It was made clear from the above that the parakeratosis caused by sebum is one mechanism by which pores become conspicuous. It was also made clear that conspicuous pores can be abated by ameliorating the parakeratosis.

In addition, as a result of searching for drugs having the above-mentioned parakeratosis-inhibiting effect and pore-shrinking effect, it was discovered that antagonists to stimulatory cell receptors and agonists to inhibitory cell receptors have these functions (see Patent Document 4). Examples of the former antagonists may include, for example, D-glutamic acid and TNP-ATP. Examples of the latter agonists may include, for example, glycine, alanine, GABA, serine, and taurine.

Nevertheless, there is a need for the development of a superior compound because no conventional compound is satisfactory as a parakeratosis inhibitor, pore-shrinking agent, or rough skin preventing/ameliorating agent in that they have insufficient effect, such as parakeratosis-inhibiting effect, pore-shrinking effect, and rough skin-preventing/ameliorating effect; they are sensory irritants; and there are limits to the amount that can be added to an external composition for skin, and the like.

Patent Document 1: Japanese Laid-Open Patent Application No. 5-97627
Patent Document 2: Japanese Laid-Open Patent Application No. 5-105619
Patent Document 3: Japanese Laid-Open Patent Application No. 2002-241260
Patent Document 4: Japanese Patent Application No. 2002-153457
Non-Patent Document 1: Yazawa et al., Aroma Research, 2002, volume 30, No. 2, p. 54-58.
Non-Patent Document 2: Iida et al., Program and Minutes of the 102$^{nd}$ Japanese Dermatological Association Convention, 2003, 103, p. 846.

DISCLOSURE OF THE INVENTION

Problems to be Solved by the Invention

The present invention was completed in light of the above-mentioned facts, and an object thereof is to provide a parakeratosis inhibitor, pore-shrinking agent, or rough skin preventing/ameliorating agent that has a function such as parakeratosis inhibition, pore shrinkage, or rough skin inhibition/abatement, poses no safety problems such as sensory irritation, and is high in safety, and to further provide an external composition for skin to which a compound having the above-mentioned function has been added.

Means Used to Solve the Above-Mentioned Problems

In order to solve the above-mentioned problems, the inventors conducted investigation and research on the compounds having an inhibiting effect on parakeratosis caused by unsaturated fatty acid based on the above-mentioned discoveries. As a result, the inventors discovered that specific β-alanine derivatives and salts thereof have the above-mentioned effect, are not sensory irritants, are high in safety, and solve the above-mentioned problems, whereby the inventors completed this invention.

Specifically, the present invention is a parakeratosis inhibitor, pore-shrinking agent, or rough skin preventing/ameliorating agent comprising one, two, or more compounds selected from β-alanine derivatives represented by the following general formula (1), (2) or (3), and salts thereof.

[Chemical formula 6]

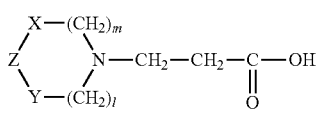
(1)

(In general formula (1), X and Y each independently represents an oxygen atom (O), nitrogen atom (N), CHQ group (in the group, Q represents a hydrogen atom (H) or a alkyl group with 1~3 carbons or hydroxyl group), or carbonyl group (C=O). Z represents a methylene group ($CH_2$), ethylene group ($CH_2$—$CH_2$), CH=CH, or a benzene ring. j and m each independently represents an integer of 0 to 5. The total of j and m, (j+m), is 0 to 6.)

[Chemical formula 7]

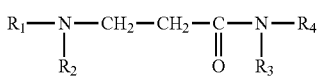
(2)

(In general formula (2), $R_1$ and $R_2$ each independently represents a hydrogen atom, alkyl group with 1~3 carbons, or alkenyl group with 1~3 carbons. $R_3$ and $R_4$ each independently represents a hydrogen atom, alkyl group with 1~3 carbons, alkenyl group with 1~3 carbons, cyclohexyl group, or a group containing nitrogen atoms and forming a cyclic structure from $R_3$ and $R_4$. The total number of carbons in $R_3$ and $R_4$ is 0 to 6.)

[Chemical formula 8]

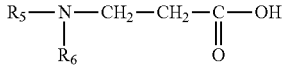
(3)

[In general formula (3), $R_5$ and $R_6$ are each independently a hydrogen atom, alkyl group with 1~7 carbons, alkenyl group with 1~7 carbons, hydrocarbon group with 3~7 carbons having a cyclic segment, pyridyl group, cyclohexyl carbonyl group, cyclopentyl carbonyl group, nicotinoyl group, isonicotinoyl group, picolinoyl group, nipecotinoyl group, isonipecotinoyl group, N-acetyl nipecotinoyl group, N-acetyl isonipecotinoyl group, benzyloxycarbonyl group, a group represented by general formula (4)

[Chemical formula 9]

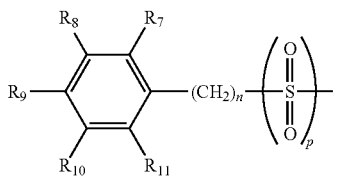
(4)

(In general formula (4), $R_7$ through $R_{11}$ each independently represents a hydrogen atom, hydroxyl group, alkyloxy group with 1~4 carbons, alkenyloxy group with 1~4 carbons, alkyl group with 1~3 carbons, or alkenyl group with 1~3 carbons; n represents an integer of 0 to 2; and p represents an integer of 0 or 1), or a group represented by general formula (5)

[Chemical formula 10]

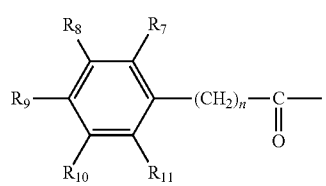
(5)

(in general formula (5), $R_7$ through $R_{11}$ and n are the same as those in general formula (4)). $R_5$ and $R_6$ cannot both be hydrogen atoms at the same time.]

X, Y, and Z in above-mentioned general formula (1) are each preferably a methylene group.

$R_1$, $R_2$, $R_3$, and $R_4$ in general formula (2) are each preferably a hydrogen atom.

One of $R_5$ and $R_6$ in general formula (3) is preferably a hydrogen atom or alkyl group with 1~3 carbons.

One of $R_5$ and $R_6$ in general formula (3) is preferably an alkyl group with 1~3 carbons, in which case the other one is preferably a hydrogen atom.

One of $R_5$ and $R_6$ in general formula (3) is preferably a hydrocarbon group with 3~7 carbons having a cyclic segment, in which case the other one is preferably a hydrogen atom or alkyl group with 1~3 carbons.

One of $R_5$ and $R_6$ in general formula (3) is preferably a pyridyl group, in which case the other one is preferably a hydrogen atom or $C_{1-3}$ alkyl group.

Preferably one of $R_5$ and $R_6$ in general formula (3) is a cyclohexylcarbonyl group, cyclopentylcarbonyl group, nicotinoyl group, isonicotinoyl group, picolinoyl group, nipecotinoyl group, isonipecotinoyl group, N-acetyl nipecotinoyl group, N-acetyl isonipecotinoyl group, or benzyloxycarbonyl group, in which case, the other one is preferably a hydrogen atom or alkyl group with 1~3 carbons.

One of $R_5$ and $R_6$ in general formula (3) is preferably a group represented by general formula (4), in which case the other one is preferably a hydrogen atom or alkyl group with 1~3 carbons. In general formula (4), preferably, p is 0 or 1; n is 0, 1, or 2; and $R_7$ through $R_{11}$ are each a hydrogen atom, or one or more of $R_7$ through $R_{11}$ are a methoxy group.

One of $R_5$ and $R_6$ in general formula (3) is preferably a group represented by general formula (5), in which case, the other one is preferably a hydrogen atom or alkyl group with 1~3 carbons. In general formula (5), preferably, p is 0 or 1; n is 0, 1, or 2; and $R_7$ through $R_{11}$ are each a hydrogen atom, or one or more of $R_7$ through $R_{11}$ are a methoxy group.

One of $R_5$ and $R_6$ in general formula (3) is preferably a methyl group, ethyl group, cyclohexyl group, cyclohexylmethyl group, benzyl group, benzenesulfonyl group, benzoyl group, 2-methoxybenzoyl group, 3-methoxybenzoyl group, 4-methoxybenzoyl group, 3,4,5-trimethoxybenzoyl group, or phenylacetyl group, in which case, the other one is preferably a hydrogen atom.

The β-alanine derivative represented by general formula (1), (2), or (3) is preferably one of 3-(1'-piperidine)-propionic acid, β-alanine amide, N-monomethyl-β-alanine, N-cyclohexyl-β-alanine, N-cyclohexylmethyl-β-alanine, N-cyclohexyl-N-methyl-β-alanine, N-cyclohexylcarbonyl-β-alanine, N-(2'-pyridyl)-β-alanine, N-nicotinoyl-β-alanine, N-benzyloxycarbonyl-β-alanine, N-benzyl-β-alanine, N-benzenesulfonyl-β-alanine, N-benzoyl-β-alanine, N-p-anisoyl-β-alanine (N-4'-methoxybenzoyl-β-alanine), N-m-anisoyl-β-alanine (N-3'-methoxybenzoyl-β-alanine), N-o-anisoyl-β-alanine (N-2'-methoxybenzoyl-β-alanine), N-3',4',5'-trimethoxybenzoyl-β-alanine, and N-phenylacetyl-β-alanine.

The above-mentioned parakeratosis inhibitor, pore-shrinking agent, or rough skin preventing/ameliorating agent of the present invention can be prepared as an external composition for skin.

Effect of the Invention

The present invention provides a very safe parakeratosis inhibitor for inhibiting parakeratosis caused by sebum; a pore-shrinking agent for inhibiting parakeratosis caused by the irritating components in the sebum around the pore, maintaining normal skin conditions around the pore, and suppressing a conical structure of the pore from becoming conspicuous; and a rough skin preventing/ameliorating agent with which rough skin caused by unsaturated fatty acids is prevented/abated. The present invention also provides an external composition for skin having a function such as inhibiting parakeratosis, shrinking pores, or preventing and ameliorating rough skin.

BEST MODE FOR CARRYING OUT THE INVENTION

The present invention is described in detail herein below.

The present invention uses one, two, or more compounds selected from β-alanine derivatives represented by the following general formula (1), (2) or (3), and salts thereof.

[Chemical formula 11]

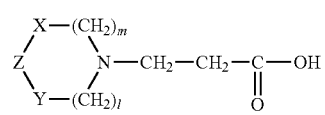

(1)

[Chemical formula 12]

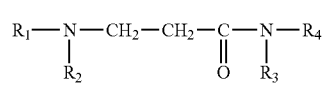

(2)

[Chemical formula 13]

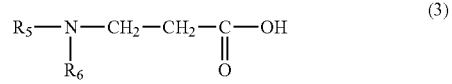

(3)

The β-alanine derivative represented by general formula (1) according to the present invention will now be described.

X and Y in general formula (1) each independently represents an oxygen atom (O), nitrogen atom (N), CHQ group (in the formula, Q is a hydrogen atom (H), alkyl group with 1~3 carbons, or hydroxyl group), or carbonyl group (C=O). Examples of the CHQ group may include, for example, $CH_2$ group, $CH(CH_3)$ group, $CH(CH_2CH_3)$ group, $CH(CH_2CH_2CH_3)$ group, $CH(CH(CH_3)_2$ group, and $CH(OH)$ group. In particular, when preferred that X and Y are each independently a methylene group ($CH_2$) or oxygen atom (O), because the compound will be easily synthesized X and Y are each as described above. In addition, X and Y are both preferably a methylene group ($CH_2$) because the effect will be good. Z is a methylene group ($CH_2$), ethylene group ($CH_2$—$CH_2$), CH=CH, or a benzene ring. When Z is a benzene ring, there is no particular restriction on the substitution position of X and Y in the benzene ring, but, the ortho position is preferred because of the effect of the present invention. In particular, Z is preferably a methylene group ($CH_2$) because of the effect of the present invention. Consequently, X, Y, and Z are each most preferably a methylene group ($CH_2$) because the effect of the present invention is good. j and m each independently represents an integer of 0 to 5. The total of j and m, (j+m), is 0 to 6. In particular, when the total of j and m, (j+m), is 1 to 4, because the effect of the present invention will be good, it is most preferably in this range.

Examples of the β-alanine derivative represented by general formula (1) may include, for example, 3-(2'-piperidone)-propionic acid, 3-(4'-piperidone)-propionic acid, 3-(2'-pyrrolidone)-propionic acid, 3-(2'-hydroxypiperidine)-propionic acid, 3-(3'-hydroxypiperidine)-propionic acid, 3-(4'-hydroxypiperidine)-propionic acid, 3-(2'-oxo-1'-hexamethyleneiminyl)-propionic acid, 3-(1'-pyrrolidine)-propionic acid, 3-(1'-piperidine)-propionic acid, 3-(1'-hexamethyleneiminyl)-propionic acid, 3-morpholinopropionic acid, 3-(piperazine-1'-yl)propionic acid, 3-(2',5'-dioxo-1'-pyrrolidine-1'-yl)propionic acid, 3-(2',6'-dioxo-'-piperidine-1'-yl) propionic acid, 3-(1'-aza-2',5'-dioxo-3'-cyclopenten-1'-yl) propionic acid, N-(2'-carboxyethyl)phthalimide, and the like. 3-(1'-pyrrolidine)-propionic acid, 3-(1'-piperidine)-propionic acid, 3-(1'-hexamethyleneiminyl)-propionic acid, 3-morpholinopropionic acid, 3-(2',5'-dioxo-1'-pyrrolidine-1'-yl)propionic acid, 3-(2',6'-dioxo-1'-piperidine-1'-yl)propionic acid, 3-(1'-aza-2',5'-dioxo-3'-cyclopenten-1'-yl)propionic acid, N-(2'-carboxyethyl)phthalimide, and the like are preferred because the effect of the present invention will be good.

The β-alanine derivative represented by general formula (2) according to the present invention will now be described.

$R_1$ and $R_2$ in general formula (2) are each independently a hydrogen atom, alkyl group with 1~3 carbons, or alkenyl group with 1~3 carbons. Examples of alkyl or alkenyl group with 1~3 carbons may include, for example, a methyl group, ethyl group, n-propyl group, iso-propyl group, allyl group, and the like. It is preferred that one or both of $R_1$ and $R_2$ are a hydrogen atom because the effect of the present invention will be good. It is further preferred that they both be a hydrogen atom.

R₃ and R₄ each independently represents a hydrogen atom, alkyl group with 1~3 carbons, alkenyl group with 1~3 carbons, cyclohexyl group, or a group containing nitrogen atoms and forming a cyclic structure from R₃ and R₄. The total number of carbon atoms in R₃ and R₄ is 0 to 6. Examples of alkyl or alkenyl group with 1~3 carbons may include, for example, a methyl group, ethyl group, n-propyl group, iso-propyl group, and allyl group. Examples of the group containing nitrogen atoms and forming a cyclic structure from R₃ and R₄ may include, for example, a pyrrolidinyl group, piperidinyl group, hexamethyleneiminyl group, and the like. It is preferred that one or both of R₃ and R₄ be a hydrogen atom because the effects of the present invention will be good. It is further preferred that they both be a hydrogen atom. It is most preferable that each of R₁, R₂, R₃, and R₄ in general formula (2) be a hydrogen atom.

Examples of the β-alanine derivative represented by general formula (2) may include, for example, β-alanine amide, β-alanine methylamine amide, β-alanine dimethylamine amide, β-alanine ethylamine amide, β-alanine diethylamine amide, β-alanine(N'-methyl-N'-ethylamine)amide, β-alanine n-propylamine amide, β-alanine di-n-propylamine amide, β-alanine(N'-methyl-N'-n-propylamine)amide, β-alanine (N'-ethyl-N'-n-propylamine)amide, β-alanine iso-propylamine amide, β-alanine di-iso-propylamine amide, β-alanine (N'-methyl-N'-iso-propylamine)amide, β-alanine (N'-ethyl-N'-iso-propylamine)amide, β-alanine(N'-n-propyl-N'-iso-propylamine)amide, β-alanine allylamine amide, β-alanine diallylamine amide, β-alanine(N'-methyl-N'-allylamine)amide, β-alanine-N-ethyl-N'-allylamine)amide, β-alanine(N'-n-propyl-N'-allylamine)amide, β-alanine(N'-iso-propyl-N'-allylamine)amide, β-alanine cyclohexylamine amide, β-alanine piperidine amide, β-alanine pyrrolidine amide, β-alanine hexamethylene imine amide, N-methyl-3-aminopropionic acid amide, N-methyl-3-aminopropionic acid methylamine amide, N-methyl-3-aminopropionic acid dimethylamine amide, N-methyl-3-aminopropionic acid ethylamine amide, N-methyl-3-aminopropionic acid diethylamine amide, N-methyl-3-aminopropionic acid (N'-methyl-N'-ethylamine)amide, N-methyl-3-aminopropionic acid n-propylamine amide, N-methyl-3-aminopropionic acid di-n-propylamine amide, N-methyl-3-aminopropionic acid (N'-methyl-N'-n-propylamine)amide, N-methyl-3-aminopropionic acid (N'-ethyl-N'-n-propylamine)amide, N-methyl-3-aminopropionic acid iso-propylamine amide, N-methyl-3-aminopropionic acid di-iso-propylamine amide, N-methyl-3-aminopropionic acid (N'-methyl-N'-iso-propylamine)amide, N-methyl-3-aminopropionic acid (N'-ethyl-N'-iso-propylamine)amide, N-methyl-3-aminopropionic acid (N'-n-propyl-N'-iso-propylamine)amide, N-methyl-3-aminopropionic acid allylamine amide, N-methyl-3-aminopropionic acid diallylamine amide, N-methyl-3-aminopropionic acid (N'-methyl-N'-allylamine)amide, N-methyl-3-aminopropionic acid (N'-ethyl-N'-allylamine)amide, N-methyl-3-aminopropionic acid (N'-n-propyl-N'-allylamine)amide, N-methyl-3-aminopropionic acid (N'-iso-propyl-N'-allylamine)amide, N-methyl-3-aminopropionic acid cyclohexylamine amide, N-methyl-3-aminopropionic acid piperidine amide, N-methyl-3-aminopropionic acid pyrrolidine amide, N-methyl-3-aminopropionic acid hexamethylene imine amide, N-ethyl-3-aminopropionic acid amide, N-ethyl-3-aminopropionic acid methyl amide, N-ethyl-3-aminopropionic acid dimethylamine amide, N-ethyl-3-aminopropionic acid ethylamine amide, N-ethyl-3-aminopropionic acid diethylamine amide, N-ethyl-3-aminopropionic acid (N'-methyl-N'-ethylamine) amide, N-ethyl-3-aminopropionic acid n-propylamine amide, N-ethyl-3-aminopropionic acid di-n-propylamine amide, N-ethyl-3-aminopropionic acid (N'-methyl-N'-n-propylamine)amide, N-ethyl-3-aminopropionic acid (N'-ethyl-N'-n-propylamine)amide, N-ethyl-3-aminopropionic acid iso-propylamine amide, N-ethyl-3-aminopropionic acid di-iso-propylamine amide, N-ethyl-3-aminopropionic acid (N'-methyl-N'-iso-propylamine)amide, N-ethyl-3-aminopropionic acid (N'-ethyl-N'-iso-propylamine)amide, N-ethyl-3-aminopropionic acid (N'-n-propyl-N'-iso-propylamine)amide, N-ethyl-3-aminopropionic acid allylamine amide, N-ethyl-3-aminopropionic acid diallylamine amide, N-ethyl-3-aminopropionic acid (N'-methyl-N'-allylamine) amide, N-ethyl-3-aminopropionic acid (N'-ethyl-N'-allylamine)amide, N-ethyl-3-aminopropionic acid (N'-n-propyl-N'-allylamine)amide, N-ethyl-3-aminopropionic acid (N'-iso-propyl-N'-allylamine)amide, N-ethyl-3-aminopropionic acid cyclohexylamine amide, N-ethyl-3-aminopropionic acid piperidine amide, N-ethyl-3-aminopropionic acid pyrrolidine amide, N-ethyl-3-aminopropionic acid hexamethylene imine amide, N-n-propyl-3-aminopropionic acid amide, N-n-propyl-3-aminopropionic acid methyl amide, N-n-propyl-3-aminopropionic acid dimethylamine amide, N-n-propyl-3-aminopropionic acid ethylamine amide, N-n-propyl-3-aminopropionic acid diethylamine amide, N-n-propyl-3-aminopropionic acid (N'-methyl-N'-ethylamine)amide, N-n-propyl-3-aminopropionic acid n-propylamine amide, N-n-propyl-3-aminopropionic acid di-n-propylamine amide, N-n-propyl-3-aminopropionic acid (N'-methyl-N'-n-propylamine)amide, N-n-propyl-3-aminopropionic acid (N'-ethyl-N'-n-propylamine)amide, N-n-propyl-3-aminopropionic acid iso-propylamine amide, N-n-propyl-3-aminopropionic acid di-iso-propylamine amide, N-n-propyl-3-aminopropionic acid (N'-methyl-N'-iso-propylamine)amide, N-n-propyl-3-aminopropionic acid (N'-ethyl-N'-iso-propylamine) amide, N-n-propyl-3-aminopropionic acid (N'-n-propyl-N'-iso-propylamine)amide, N-n-propyl-3-aminopropionic acid allylamine amide, N-n-propyl-3-aminopropionic acid diallylamine amide, N-n-propyl-3-aminopropionic acid (N'-methyl-N'-allylamine)amide, N-n-propyl-3-aminopropionic acid (N'-ethyl-N'-allylamine)amide, N-n-propyl-3-aminopropionic acid (N'-n-propyl-N'-allylamine)amide, N-n-propyl-3-aminopropionic acid (N'-iso-propyl-N'-allylamine) amide, N-n-propyl-3-aminopropionic acid cyclohexylamine amide, N-n-propyl-3-aminopropionic acid piperidine amide, N-n-propyl-3-aminopropionic acid pyrrolidine amide, N-n-propyl-3-aminopropionic acid hexamethyleneimine amide, N-iso-propyl-3-aminopropionic acid amide, N-iso-propyl-3-aminopropionic acid methyl amide, N-iso-propyl-3-aminopropionic acid dimethylamine amide, N-iso-propyl-3-aminopropionic acid ethylamine amide, N-iso-propyl-3-aminopropionic acid diethylamine amide, N-iso-propyl-3-aminopropionic acid (N'-methyl-N'-ethylamine)amide, N-iso-propyl-3-aminopropionic acid n-propylamine amide, N-iso-propyl-3-aminopropionic acid di-n-propylamine amide, N-iso-propyl-3-aminopropionic acid (N'-methyl-N'-n-propylamine)amide, N-iso-propyl-3-aminopropionic acid (N'-ethyl-N'-n-propylamine)amide, N-iso-propyl-3-aminopropionic acid iso-propylamine amide, N-iso-propyl-3-aminopropionic acid di-iso-propylamine amide, N-iso-propyl-3-aminopropionic acid (N'-methyl-N'-iso-propylamine)amide, N-iso-propyl-3-aminopropionic acid (N'-ethyl-N'-iso-propylamine)amide, N-iso-propyl-3-aminopropionic acid (N'-ethyl-N'-iso-propylamine)amide, N-iso-propyl-3-aminopropionic acid (N'-n-propyl-N'-iso-propylamine)amide, N-iso-propyl-3-aminopropionic acid allylamine amide, N-iso-propyl-3-aminopropionic acid diallylamine amide, N-iso-propyl-3-aminopropionic acid (N'-methyl-N'-allylamine)amide, N-iso-propyl-3-aminopropionic acid (N'-ethyl-N'-allylamine) amide, N-iso-propyl-3-aminopropionic acid (N'-n-propyl-N'-allylamine)amide, N-iso-propyl-3-aminopropionic acid (N'-iso-propyl-N'-allylamine)amide, N-iso-propyl-3-aminopropionic acid cyclohexylamine amide, N-iso-propyl-3-aminopropionic acid piperidine amide, N-iso-propyl-3-aminopropionic acid pyrrolidine amide, N-iso-propyl-3-aminopropionic acid hexamethyleneimine amide, N-allyl-3-aminopropionic acid amide, N-allyl-3-aminopropionic acid methyl amide, N-allyl-3-aminopropionic acid dimethylamine amide, N-allyl-3-aminopropionic acid ethylamine amide, N-allyl-3-aminopropionic acid diethylamine amide, N-allyl-3-aminopropionic acid (N'-methyl-N'-ethylamine)amide, N-allyl-3-aminopropionic acid n-propylamine amide, N-allyl-3-aminopropionic acid di-n-propylamine amide, N-allyl-3-aminopropionic acid (N'-methyl-N'-n-propylamine)amide, N-allyl-3-aminopropionic acid (N'-ethyl-N'-n-propylamine)amide, N-allyl-3-aminopropionic acid iso-propylamine amide, N-allyl-3-aminopropionic acid di-iso-propylamine amide, N-allyl-3-aminopropionic acid (N'-methyl-N'-iso-propylamine)amide, N-allyl-3-aminopropionic acid (N'-ethyl-N'-iso-propylamine)amide, N-allyl-3-aminopropionic acid (N'-n-propyl-N'-iso-propylamine)amide, N-allyl-3-aminopropionic acid allylamine amide, N-allyl-3-aminopropionic acid diallylamine amide, N-allyl-3-aminopropionic acid (N'-methyl-N'-allylamine) amide, N-allyl-3-aminopropionic acid (N'-ethyl-N'-allylamine)amide, N-allyl-3-aminopropionic acid (N'-n-propyl-N'-allylamine)amide, N-allyl-3-aminopropionic acid (N'-iso-propyl-N'-allylamine)amide, N-allyl-3-aminopropionic acid cyclohexylamine amide, N-allyl-3-aminopropionic acid piperidine amide, N-allyl-3-aminopropionic acid pyrrolidine amide, N-allyl-3-aminopropionic acid hexamethyleneimine amide, N,N-dimethyl-3-aminopropionic acid amide, N,N-dimethyl-3-aminopropionic acid methyl amide, N,N-dimethyl-3-aminopropionic acid dimethylamine amide, N,N-dimethyl-3-aminopropionic acid ethylamine amide, N,N-dimethyl-3-aminopropionic acid diethylamine amide, N,N-dimethyl-3-aminopropionic acid (N'-methyl-N'-ethylamine)amide, N,N-dimethyl-3-aminopropionic acid n-propylamine amide, N,N-dimethyl-3-aminopropionic acid di-n-propylamine amide, N,N-dimethyl-3-aminopropionic acid (N'-methyl-N'-n-propylamine)amide, N,N-dimethyl-3-aminopropionic acid (N'-ethyl-N'-n-propylamine)amide, N,N-dimethyl-3-aminopropionic acid iso-propylamine amide, N,N-dimethyl-3-aminopropionic acid di-iso-propylamine amide, N,N-dimethyl-3-aminopropionic acid (N'-methyl-N'-iso-propylamine)amide, N,N-dimethyl-3-aminopropionic acid (N'-ethyl-N'-iso-propylamine)amide, N,N-dimethyl-3-aminopropionic acid (N'-n-propyl-N'-iso-propylamine)amide, N,N-dimethyl-3-aminopropionic acid allylamine amide, N,N-dimethyl-3-aminopropionic acid diallylamine amide, N,N-dimethyl-3-aminopropionic acid (N'-methyl-N'-allylamine)amide, N,N-dimethyl-3-aminopropionic acid (N'-ethyl-N'-allylamine)amide, N,N-dimethyl-3-aminopropionic acid (N'-n-propyl-N'-allylamine)amide, N,N-dimethyl-3-aminopropionic acid (N'-iso-propyl-N'-allylamine)amide, N,N-dimethyl-3-aminopropionic acid cyclohexylamine amide, N,N-dimethyl-3-aminopropionic acid piperidine amide, N,N-dimethyl-3-aminopropionic acid pyrrolidine amide, N,N-dimethyl-3-aminopropionic acid hexamethyleneimine amide, N,N-diethyl-3-aminopropionic acid amide, N,N-diethyl-3-aminopropionic acid methyl amide, N,N-diethyl-3-aminopropionic acid dimethylamine amide, N,N-diethyl-3-aminopropionic acid ethylamine amide, N,N-diethyl-3-aminopropionic acid diethylamine amide, N,N-diethyl-3-aminopropionic acid (N'-methyl-N'-ethylamine)amide, N,N-diethyl-3-aminopropionic acid n-propylamine amide, N,N-diethyl-3-aminopropionic acid di-n-propylamine amide, N,N-diethyl-3-aminopropionic acid (N'-methyl-N'-n-propylamine)amide, N,N-diethyl-3-aminopropionic acid (N'-ethyl-N'-n-propylamine)amide, N,N-diethyl-3-aminopropionic acid iso-propylamine amide, N,N-diethyl-3-aminopropionic acid di-iso-propylamine amide, N,N-diethyl-3-aminopropionic acid (N'-methyl-N'-iso-propylamine)amide, N,N-diethyl-3-aminopropionic acid (N'-ethyl-N'-iso-propylamine)amide, N,N-diethyl-3-aminopropionic acid (N'-n-propyl-N'-iso-propylamine)amide, N,N-diethyl-3-aminopropionic acid allylamine amide, N,N-diethyl-3-aminopropionic acid diallylamine amide, N,N-diethyl-3-aminopropionic acid (N'-methyl-N'-allylamine)amide, N,N-diethyl-3-aminopropionic acid (N'-ethyl-N'-allylamine)amide, N,N-diethyl-3-aminopropionic acid (N'-n-propyl-N'-allylamine)amide, N,N-diethyl-3-aminopropionic acid (N'-iso-propyl-N'-allylamine)amide, N,N-diethyl-3-aminopropionic acid cyclohexylamine amide, N,N-diethyl-3-aminopropionic acid piperidine amide, N,N-diethyl-3-aminopropionic acid pyrrolidine amide, N,N-diethyl-3-aminopropionic acid hexamethyleneimine amide, N-ethyl-N-methyl-3-aminopropionic acid amide, N-ethyl-N-methyl-3-aminopropionic acid methylamine amide, N-ethyl-N-methyl-3-aminopropionic acid dimethylamine amide, N-ethyl-N-methyl-3-aminopropionic acid ethylamine amide, N-ethyl-N-methyl-3-aminopropionic acid diethylamine amide, N-ethyl-N-methyl-3-aminopropionic acid (N'-methyl-N'-ethylamine)amide, N-ethyl-N-methyl-3-aminopropionic acid n-propylamine amide, N-ethyl-N-methyl-3-aminopropionic acid di-n-propylamine amide, N-ethyl-N-methyl-3-aminopropionic acid (N'-methyl-N'-n-propylamine)amide, N'-ethyl-N-methyl-3-aminopropionic acid (N'-ethyl-N'-n-propylamine)amide, N-ethyl-N-methyl-3-aminopropionic acid iso-propylamine amide, N,N-d(n-propyl)-3-aminopropionic acid n-propylamine amide, N-ethyl-N-methyl-3-aminopropionic acid di-iso-propylamine amide, N-ethyl-N-methyl-3-aminopropionic acid (N'-methyl-N'-iso-propylamine)amide, N-ethyl-N-methyl-3-aminopropionic acid (N'-ethyl-N'-iso-propylamine)amide, N-ethyl-N-methyl-3-aminopropionic acid (N'-n-propyl-N'-iso-propylamine)amide, N-ethyl-N-methyl-3-aminopropionic acid allylamine amide, N-ethyl-N-methyl-3-aminopropionic acid diallylamine amide, N-ethyl-N-methyl-3-aminopropionic acid (N'-methyl-N'-allylamine)amide, N-ethyl-N-methyl-3-aminopropionic acid (N'-ethyl-N'-allylamine)amide, N-ethyl-N-methyl-3-aminopropionic acid (N'-n-propyl-N'-allylamine)amide, N-ethyl-N-methyl-3-aminopropionic acid (N'-iso-propyl-N'-allylamine)amide, N-ethyl-N-methyl-3-aminopropionic acid cyclohexylamine amide, N-ethyl-N-methyl-3-aminopropionic acid piperidine amide, N-ethyl-N-methyl-3-aminopropionic acid pyrrolidine amide, N-ethyl-N-methyl-3-aminopropionic acid hexamethyleneimine amide, N,N-di(n-propyl)-3-aminopropionic acid amide, N,N-di(n-propyl)-3-aminopropionic acid methyl amide, N,N-di(n-propyl)-3-aminopropionic acid dimethylamine amide, N,N-di(n-propyl)-3-aminopropionic acid ethylamine amide, N,N-di(n-propyl)-3-aminopropionic acid diethylamine amide, N,N-di(n-propyl)-3-aminopropionic acid (N'-methyl-N'-ethylamine)amide, N,N-di(n-propyl)-3-aminopropionic acid di-n-propylamine amide, N,N-di(n-propyl)-3-aminopropionic acid (N'-methyl-N'-n-propylamine)amide, N,N-di(n-propyl)-3-aminopropionic acid (N'-ethyl-N'-n-propylamine)amide, N,N-di(n-propyl)-3-aminopropionic acid iso-propylamine amide, N,N-di(n-propyl)-3-aminopropionic acid di-iso-propylamine amide, N,N-di(n-propyl)-3-aminopropionic acid (N'-methyl-N'-iso-propylamine)amide, N,N-di(n-propyl)-3-aminopropionic acid (N'-ethyl-N'-iso-propylamine)amide, N,N-di(n-propyl)-3-aminopropionic acid (N'-n-propyl-N'-iso-propylamine)amide, N,N-di(n-propyl)-3-aminopropionic acid allylamine amide, N,N-di(n-propyl)-3-aminopropionic acid diallylamine amide, N,N-di(n-propyl)-3-aminopropionic acid (N'-methyl-N'-allylamine)amide, N,N-di(n-propyl)-3-aminopropionic acid (N'-ethyl-N'-allylamine)amide, N,N-di(n-propyl)-3-aminopropionic acid (N'-n-propyl-N'-allylamine)amide, N,N-di(n-propyl)-3-aminopropionic acid (N'-iso-propyl-N'-allylamine)amide, N,N-di(n-propyl)-3-aminopropionic acid cyclohexylamine amide, N,N-di(n-propyl)-3-aminopropionic acid piperidine amide, N,N-di(n-propyl)-3-aminopropionic acid pyrrolidine amide, N,N-di(n-propyl)-3-aminopropionic acid hexamethyleneimine amide, N-n-propyl-N-methyl-3-aminopropionic acid amide, N-n-propyl-N-methyl-3-aminopropionic acid methyl amide, N-n-propyl-N-methyl-3-aminopropionic acid dimethylamine amide, N-n-propyl-N-methyl-3-aminopropionic acid ethylamine amide, N-n-propyl-N-methyl-3-aminopropionic acid diethylamine amide, N-n-propyl-N-methyl-3-aminopropionic acid (N'-methyl-N'-ethylamine)amide, N-n-propyl-N-methyl-3-aminopropionic acid n-propylamine amide, N-n-propyl-N-methyl-3-aminopropionic acid di-n-propylamine amide, N-n-propyl-N-methyl-3-aminopropionic acid (N'-methyl-N'-n-propylamine)amide, N-n-propyl-N-methyl-3-aminopropionic acid (N'-ethyl-N'-n-propylamine)amide, N-n-propyl-N-methyl-3-aminopropionic acid iso-propylamine amide, N-n-propyl-N-methyl-3-aminopropionic acid di-iso-propylamine amide, N-n-propyl-N-methyl-3-aminopropionic acid (N'-methyl-N'-iso-propylamine)amide, N-n-propyl-N-methyl-3-aminopropionic acid (N'-ethyl-N'-iso-propylamine)amide, N-n-propyl-N-methyl-3-aminopropionic acid (N'-n-propyl-N'-iso-propylamine) amide, N-n-propyl-N-methyl-3-aminopropionic acid allylamine amide, N-n-propyl-N-methyl-3-aminopropionic acid diallylamine amide, N-n-propyl-N-methyl-3-aminopropionic acid (N'-methyl-N'-allylamine)amide, N-n-propyl-N-methyl-3-aminopropionic acid (N'-ethyl-N'-allylamine) amide, N-n-propyl-N-methyl-3-aminopropionic acid (N'-n-propyl-N'-allylamine)amide, N-n-propyl-N-methyl-3-aminopropionic acid (N'-iso-propyl-N'-allylamine)amide, N-n-propyl-N-methyl-3-aminopropionic acid cyclohexylamine amide, N-n-propyl-N-methyl-3-aminopropionic acid piperidine amide, N-n-propyl-N-methyl-3-aminopropionic acid pyrrolidine amide, N-n-propyl-N-methyl-3-aminopropionic acid hexamethyleneimine amide, N-ethyl-N-n-propyl-3-aminopropionic acid amide, N-ethyl-N-n-propyl-3-aminopropionic acid methylamine amide, N-ethyl-N-n-propyl-3-aminopropionic acid dimethylamine amide, N-ethyl-N-n-propyl-3-aminopropionic acid ethylamine amide, N-ethyl-N-n-propyl-3-aminopropionic acid diethylamine amide, N-ethyl-N-n-propyl-3-aminopropionic acid (N'-methyl-N'-ethylamine)amide, N-ethyl-N-n-propyl-3-aminopropionic acid n-propylamine amide, N-ethyl-N-n-propyl-3-aminopropionic acid di-n-propylamine amide, N-ethyl-N-n-propyl-3-aminopropionic acid (N'-methyl-N'-n-propylamine)amide, N-ethyl-N-n-propyl-3-aminopropionic acid (N'-ethyl-N'-n-propylamine)amide, N-ethyl-N-n-propyl-3-aminopropionic acid iso-propylamine amide, N-ethyl-N-n-propyl-3-aminopropionic acid di-iso-propylamine amide, N-ethyl-N-n-propyl-3-aminopropionic acid (N'-methyl-N'-iso-propylamine) amide, N-ethyl-N-n-propyl aminopropionic acid (N'-ethyl-N'-iso-propylamine)amide, N-ethyl-N-n-propyl-3-aminopropionic acid (N'-n-propyl-N'-iso-propylamine) amide, N-ethyl-N-n-propyl-3-aminopropionic acid allylamine amide, N-ethyl-N-n-propyl-3-aminopropionic acid diallylamine amide, N-ethyl-N-n-propyl-3-aminopropionic acid (N-methyl-N'-allylamine)amide, N-ethyl-N-n-propyl-3-aminopropionic acid (N'-ethyl-N'-allylamine)amide, N-ethyl-N-n-propyl-3-aminopropionic acid (N'-n-propyl-N'-allylamine) amide, N-ethyl-N-n-propyl-3-aminopropionic acid (N'-iso-propyl-N'-allylamine)amide, N-ethyl-N-n-propyl-3-aminopropionic acid cyclohexylamine amide, N-ethyl-N-n-propyl-3-aminopropionic acid piperidine amide, N-ethyl-N-n-propyl-3-aminopropionic acid pyrrolidine amide, N-ethyl-N-n-propyl-3-aminopropionic acid hexamethyleneimine amide, N,N-di(iso-propyl)-3-aminopropionic acid amide, N,N-di(iso-propyl)-3-aminopropionic acid methyl amide, N,N-di(iso-propyl)-3-aminopropionic acid dimethylamine amide, N,N-di(iso-propyl)-3-aminopropionic acid ethylamine amide, N,N-di(iso-propyl)-3-aminopropionic acid diethylamine amide, N,N-di(iso-propyl)-3-aminopropionic acid (N'-methyl-N'-ethylamine)amide, N,N-di(iso-propyl)-3-aminopropionic acid n-propylamine amide, N,N-di(iso-propyl)-3-aminopropionic acid di-n-propylamine amide, N,N-di(iso-propyl)-3-aminopropionic acid (N'-methyl-N'-n-propylamine)amide, N,N-di(iso-propyl)-3-aminopropionic acid (N'-ethyl-N'-n-propylamine)amide, N,N-di(iso-propyl)-3-aminopropionic acid iso-propylamine amide, N,N-di(iso-propyl)-3-aminopropionic acid di-iso-propylamine amide, N,N-di(iso-propyl)-3-aminopropionic acid (N'-methyl-N'-iso-propylamine)amide, N,N-di(iso-propyl)-3-aminopropionic acid (N'-ethyl-N'-iso-propylamine)amide, N,N-di(iso-propyl)-3-aminopropionic acid (N'-n-propyl-N'-iso-propylamine)amide, N,N-di(iso-propyl)-3-aminopropionic acid allylamine amide, N,N-di(iso-propyl)-3-aminopropionic acid diallylamine amide, N,N-di(iso-propyl)-3-aminopropionic acid (N'-methyl-N'-allylamine)amide, N,N-di(iso-propyl)-3-aminopropionic acid (N'-ethyl-N'-allylamine) amide, N,N-di(iso-propyl)-3-aminopropionic acid (N'-n-propyl-N-allylamine)amide, N,N-di(iso-propyl)-3-aminopropionic acid (N'-iso-propyl-N-allylamine)amide, N,N-di(iso-propyl)-3-aminopropionic acid cyclohexylamine amide, N,N-di(iso-propyl)-3-aminopropionic acid piperidine amide, N,N-di(iso-propyl)-3-aminopropionic acid pyrrolidine amide, N,N-di(iso-propyl)-3-aminopropionic acid hexamethyleneimine amide, N-iso-propyl-N-methyl-3-aminopropionic acid amide, N-iso-propyl-N-methyl-3-aminopropionic acid methylamine amide, N-iso-propyl-N-methyl-3-aminopropionic acid dimethylamine amide, N-iso-propyl-N-methyl-3-aminopropionic acid ethylamine amide, N-iso-propyl-N-methyl-3-aminopropionic acid diethylamine amide, N-iso-propyl-N-methyl-3-aminopropionic acid (N'-methyl-N'-ethylamine)amide, N-iso-propyl-N-methyl-3-aminopropionic acid n-propylamine amide, N-iso-propyl-N-methyl-3-aminopropionic acid di-n-propylamine amide, N-iso-propyl-N-methyl-3-aminopropionic acid (N'-methyl-N'-n-propylamine)amide, N-iso-propyl-N-methyl-3-aminopropionic acid (N'-ethyl-N'-n-propylamine)amide, N-iso-propyl-N-methyl-3-aminopropionic acid iso-propylamine amide, N-iso-propyl-N-methyl-3-aminopropionic acid di-iso-propylamine amide, N-iso-propyl-N-methyl-3-aminopropionic acid (N'-methyl-N'-iso-propylamine)amide, N-iso-propyl-N-methyl-3-aminopropionic acid (N'-ethyl-N'-iso-propylamine)amide, N-iso-propyl-N-methyl-3-aminopropionic acid (N'-n-propyl-N'-iso-propylamine)amide, N-iso-propyl-N-methyl-3-aminopropionic acid allylamine amide, N-iso-propyl-N-methyl-3-aminopropionic acid diallylamine amide, N-iso-propyl-N-methyl-3-aminopropionic acid (N'-methyl-N'-allylamine)amide, N-iso-propyl-N-methyl-3-aminopropionic acid (N'-ethyl-N-allylamine)amide, N-iso-propyl-N-methyl-3-aminopropionic acid (N'-n-propyl-N'-allylamine)amide, N-iso-propyl-N-methyl-3-aminopropionic acid (N'-iso-propyl-N'-allylamine)amide, N-iso-propyl-N-methyl-3-aminopropionic acid cyclohexylamine amide, N-iso-propyl-N-methyl-3-aminopropionic acid piperidine amide, N-iso-propyl-N-methyl-3-aminopropionic acid pyrrolidine amide, N-iso-propyl-N-methyl-3-aminopropionic acid hexamethyleneimine amide, N-ethyl-N-iso-propyl-3-aminopropionic acid amide, N-ethyl-N-iso-propyl-3-aminopropionic acid methylamine amide, N-ethyl-N-iso-propyl-3-aminopropionic acid dimethylamine amide, N-ethyl-N-iso-propyl-3-aminopropionic acid ethylamine amide, N-ethyl-N-iso-propyl-3-aminopropionic acid diethylamine amide, N-ethyl-N-iso-propyl-3-aminopropionic acid (N'-methyl-N'-ethylamine)amide, N-ethyl-N-iso-propyl-3-aminopropionic acid n-propylamine amide, N-ethyl-N-iso-propyl-3-aminopropionic acid di-n-propylamine amide, N-ethyl-N-iso-propyl-3-aminopropionic acid (N'-methyl-N'-n-propylamine)amide, N-ethyl-N-iso-propyl-3-aminopropionic acid (N'-ethyl-N'-n-propylamine)amide, N-ethyl-N-iso-propyl-3-aminopropionic acid iso-propylamine amide, N-ethyl-N-iso-propyl-3-aminopropionic acid di-iso-propylamine amide, N-ethyl-N-iso-propyl-3-aminopropionic acid (N'-methyl-N'-iso-propylamine)amide, N-ethyl-N-iso-propyl-3-aminopropionic acid (N'-ethyl-N-iso-propylamine)amide, N-ethyl-N-iso-propyl-3-aminopropionic acid (N'-n-propyl-N'-iso-propylamine)amide, N-ethyl-N-iso-propyl-3-aminopropionic acid allylamine amide, N-ethyl-N-iso-propyl-3-aminopropionic acid diallylamine amide, N-ethyl-N-iso-propyl-3-aminopropionic acid (N'-methyl-N'-allylamine)amide, N-ethyl-N-iso-propyl-3-aminopropionic acid (N'-ethyl-N'-allylamine)amide, N-ethyl-N-iso-propyl-3-aminopropionic acid (N'-n-propyl-N'-allylamine)amide, N-ethyl-N-iso-propyl-3-aminopropionic acid (N'-iso-propyl-N'-allylamine)amide, N-ethyl-N-iso-propyl-3-aminopropionic acid cyclohexylamine amide, N-ethyl-N-iso-propyl-3-aminopropionic acid piperidine amide, N-ethyl-N-iso-propyl-3-aminopropionic acid pyrrolidine amide, N-ethyl-N-iso-propyl-3-aminopropionic acid hexamethyleneimine amide, N-n-propyl-N-iso-propyl-3-aminopropionic acid amide, N-n-propyl-N-iso-propyl-3-aminopropionic acid methylamine amide, N-n-propyl-N-iso-propyl-3-aminopropionic acid dimethylamine amide, N-n-propyl-N-iso-propyl-3-aminopropionic acid ethylamine amide, N-n-propyl-N-iso-propyl-3-aminopropionic acid diethylamine amide, N-n-propyl-N-iso-propyl-3-aminopropionic acid (N'-methyl-N'-ethylamine)amide, N-n-propyl-N-iso-propyl-3-aminopropionic acid n-propylamine amide, N-n-propyl-N-iso-propyl-3-aminopropionic acid di-n-propylamine amide, N-n-propyl-N-iso-propyl-3-aminopropionic acid (N'-methyl-N'-n-propylamine)amide, N-n-propyl-N-iso-propyl-3-aminopropionic acid (N'-ethyl-N-n-propylamine)amide, N-n-propyl-N-iso-propyl-3-aminopropionic acid iso-propylamine amide, N-n-propyl-N-iso-propyl-3-aminopropionic acid di-iso-propylamine amide, N-n-propyl-N-iso-propyl-3-aminopropionic acid (N'-methyl-N'-iso-propylamine)amide, N-n-propyl-N-iso-propyl-3-aminopropionic acid (N'-ethyl-N'-iso-propylamine)amide, N-n-propyl-N-iso-propyl-3-aminopropionic acid (N'-n-propyl-N'-iso-propylamine) amide, N-n-propyl-N-iso-propyl-3-aminopropionic acid allylamine amide, N-n-propyl-N-iso-propyl-3-aminopropionic acid diallylamine amide, N-n-propyl-N-iso-propyl-3-aminopropionic acid (N'-methyl-N'-allylamine)amide, N-n-propyl-N-iso-propyl-3-aminopropionic acid (N'-ethyl-N'-allylamine)amide, N-n-propyl-N-iso-propyl-3-aminopropionic acid (N'-n-propyl-N'-allylamine)amide, N-n-propyl-N-iso-propyl-3-aminopropionic acid (N'-iso-propyl-N'-allylamine)amide, N-n-propyl-N-iso-propyl-3-aminopropionic acid cyclohexylamine amide, N-n-propyl-N-iso-propyl-3-aminopropionic acid piperidine amide, N-n-propyl-N-iso-propyl-3-aminopropionic acid pyrrolidine amide, N-n-propyl-N-iso-propyl-3-aminopropionic acid hexamethyleneimine amide, N,N-diallyl-3-aminopropionic acid amide, N,N-diallyl-3-aminopropionic acid methyl amide, N,N-diallyl-3-aminopropionic acid dimethylamine amide, N,N-diallyl-3-aminopropionic acid ethylamine amide, N,N-diallyl-3-aminopropionic acid diethylamine amide, N,N-diallyl-3-aminopropionic acid (N'-methyl-N-ethylamine)amide, N,N-diallyl-3-aminopropionic acid n-propylamine amide, N,N-diallyl-3-aminopropionic acid di-n-propylamine amide, N,N-diallyl-3-aminopropionic acid (N-methyl-N-n-propylamine)amide, N,N-diallyl-3-aminopropionic acid (N'-ethyl-N-n-propylamine)amide, N,N-diallyl-3-aminopropionic acid iso-propylamine amide, N,N-diallyl-3-aminopropionic acid di-iso-propylamine amide, N,N-diallyl-3-aminopropionic acid (N'-methyl-N'-iso-propylamine)amide, N,N-diallyl-3-aminopropionic acid (N'-ethyl-N'-iso-propylamine)amide, N,N-diallyl-3-aminopropionic acid (N'-n-propyl-N'-iso-propylamine) amide, N,N-diallyl-3-aminopropionic acid allylamine amide, N,N-diallyl-3-aminopropionic acid diallylamine amide, N,N-diallyl-3-aminopropionic acid (N'-methyl-N'-allylamine)amide, N,N-diallyl-3-aminopropionic acid (N'-ethyl-N'-allylamine)amide, N,N-diallyl-3-aminopropionic acid (N'-n-propyl-N'-allylamine)amide, N,N-diallyl-3-aminopropionic acid (N'-iso-propyl-N'-allylamine)amide, N,N-diallyl-3-aminopropionic acid cyclohexylamine amide, N,N-diallyl-3-aminopropionic acid piperidine amide, N,N-diallyl-3-aminopropionic acid pyrrolidine amide, N,N-diallyl-3-aminopropionic acid hexamethyleneimine amide, N-allyl-N-methyl-3-aminopropionic acid amide, N-allyl-N-methyl-3-aminopropionic acid methylamine amide, N-allyl-N-methyl-3-aminopropionic acid dimethylamine amide, N-allyl-N-methyl-3-aminopropionic acid ethylamine amide, N-allyl-N-methyl-3-aminopropionic acid diethylamine amide, N-allyl-N-methyl-3-aminopropionic acid (N-methyl-N-ethylamine)amide, N-allyl-N-methyl-3-aminopropionic acid n-propylamine amide, N-allyl-N-methyl-3-aminopropionic acid di-n-propylamine amide, N-allyl-N-methyl-3-aminopropionic acid (N'-methyl-N'-n-propylamine)amide, N-allyl-N-methyl-3-aminopropionic acid (N'-ethyl-N'-n-propylamine)amide, N-allyl-N-methyl-3-aminopropionic acid iso-propylamine amide, N-allyl-N-methyl-3-aminopropionic acid di-iso-propylamine amide, N-allyl-N-methyl-3-aminopropionic acid (N'-methyl-N'-iso-propylamine)amide, N-allyl-N-methyl-3-aminopropionic acid (N'-ethyl-N'-iso-propylamine)amide, N-allyl-N-methyl-3-aminopropionic acid (N'-n-propyl-N'-iso-propylamine)amide, N-allyl-N-methyl-3-aminopropionic acid allylamine amide, N-allyl-N-methyl-3-aminopropionic acid diallylamine amide, N-allyl-N-methyl-3-aminopropionic acid (N-methyl-N-allylamine) amide, N-allyl-N-methyl-3-aminopropionic acid (N'-ethyl-N'-allylamine)amide, N-allyl-N-methyl-3-aminopropionic acid (N'-n-propyl-N'-allylamine)amide, N-allyl-N-methyl-3-aminopropionic acid (N'-iso-propyl-N'-allylamine)amide, N-allyl-N-methyl-3-aminopropionic acid cyclohexylamine amide, N-allyl-N-methyl-3-aminopropionic acid piperidine amide, N-allyl-N-methyl-3-aminopropionic acid pyrrolidine amide, N-allyl-N-methyl-3-aminopropionic acid hexamethyleneimine amide, N-allyl-N-ethyl-3-aminopropionic acid amide, N-allyl-N-ethyl-3-aminopropionic acid methylamine amide, N-allyl-N-ethyl-3-aminopropionic acid dimethylamine amide, N-allyl-N-ethyl-3-aminopropionic acid ethylamine amide, N-allyl-N-ethyl-3-aminopropionic acid diethylamine amide, N-allyl-N-ethyl-3-aminopropionic acid (N'-methyl-N'-ethylamine)amide, N-allyl-N-ethyl-3-aminopropionic acid n-propylamine amide, N-allyl-N-ethyl-3-aminopropionic acid di-n-propylamine amide, N-allyl-N-ethyl-3-aminopropionic acid (N'-methyl-N'-n-propylamine)amide, N-allyl-N-ethyl-3-aminopropionic acid (N'-ethyl-N'-n-propylamine)amide, N-allyl-N-ethyl-3-aminopropionic acid iso-propylamine amide, N-allyl-N-ethyl-3-aminopropionic acid di-iso-propylamine amide, N-allyl-N-ethyl-3-aminopropionic acid (1-methyl-N-iso-propylamine)amide, N-allyl-N-ethyl-3-aminopropionic acid (N'-ethyl-N'-iso-propylamine)amide, N-allyl-N-ethyl-3-aminopropionic acid (N'-n-propyl-N'-iso-propylamine)amide, N-allyl-N-ethyl-3-aminopropionic acid allylamine amide, N-allyl-N-ethyl-3-aminopropionic acid diallylamine amide, N-allyl-N-ethyl-3-aminopropionic acid (N-methyl-N'-allylamine)amide, N-allyl-N-ethyl-3-aminopropionic acid (N'-ethyl-N'-allylamine)amide, N-allyl-N-ethyl-3-aminopropionic acid (N'-n-propyl-N'-allylamine)amide, N-allyl-N-ethyl-3-aminopropionic acid (N'-iso-propyl-N'-allylamine)amide, N-allyl-N-ethyl-3-aminopropionic acid cyclohexylamine amide, N-allyl-N-ethyl-3-aminopropionic acid piperidine amide, N-allyl-N-ethyl-3-aminopropionic acid pyrrolidine amide, N-allyl-N-ethyl-3-aminopropionic acid hexamethyleneimine amide, N-allyl-N-n-propyl-3-aminopropionic acid amide, N-allyl-N-n-propyl-3-aminopropionic acid methylamine amide, N-allyl-N-n-propyl-3-aminopropionic acid dimethylamine amide, N-allyl-N-n-propyl-3-aminopropionic acid ethylamine amide, N-allyl-N-n-propyl-3-aminopropionic acid diethylamine amide, N-allyl-N-n-propyl-3-aminopropionic acid (N-methyl-N'-ethylamine)amide, N-allyl-N-n-propyl-3-aminopropionic acid n-propylamine amide, N-allyl-N-n-propyl-3-aminopropionic acid di-n-propylamine amide, N-allyl-N-n-propyl-3-aminopropionic acid (N'-methyl-N'-n-propylamine)amide, N-allyl-N-n-propyl-3-aminopropionic acid (N'-ethyl-N'-n-propylamine)amide, N-allyl-N-n-propyl-3-aminopropionic acid iso-propylamine amide, N-allyl-N-n-propyl-3-aminopropionic acid di-iso-propylamine amide, N-allyl-N-n-propyl-3-aminopropionic acid (N'-methyl-N'-iso-propylamine)amide, N-allyl-N-n-propyl-3-aminopropionic acid (N'-ethyl-N'-iso-propylamine)amide, N-allyl-N-n-propyl-3-aminopropionic acid (N'-n-propyl-N'-iso-propylamine)amide, N-allyl-N-n-propyl-3-aminopropionic acid allylamine amide, N-allyl-N-n-propyl-3-aminopropionic acid diallylamine amide, N-allyl-N-n-propyl-3-aminopropionic acid (N'-methyl-N'-allylamine)amide, N-allyl-N-n-propyl-3-aminopropionic acid (N'-ethyl-N'-allylamine)amide, N-allyl-N'-n-propyl-3-aminopropionic acid (N'-n-propyl-N'-allylamine)amide, N-allyl-N-n-propyl-3-aminopropionic acid (N'-iso-propyl-N'-allylamine)amide, N-allyl-N-n-propyl-3-aminopropionic acid cyclohexylamine amide, N-allyl-N-n-propyl-3-aminopropionic acid piperidine amide, N-allyl-N-n-propyl-3-aminopropionic acid pyrrolidine amide, N-ally-N-n-propyl-3-aminopropionic acid hexamethyleneimine amide, N-allyl-N-iso-propyl-3-aminopropionic acid amide, N-allyl-N-iso-propyl-3-aminopropionic acid methylamine amide, N-allyl-N-iso-propyl-3-aminopropionic acid dimethylamine amide, N-allyl-N-iso-propyl-3-aminopropionic acid ethylamine amide, N-allyl-N-iso-propyl-3-aminopropionic acid diethylamine amide, N-allyl-N-iso-propyl-3-aminopropionic acid (N'-methyl-N'-ethylamine)amide, N-allyl-N-iso-propyl-3-aminopropionic acid n-propylamine amide, N-allyl-N-iso-propyl-3-aminopropionic acid di-n-propylamine amide, N-allyl-N-iso-propyl-3-aminopropionic acid (N'-methyl-N'-n-propylamine)amide, N-allyl-N-iso-propyl-3-aminopropionic acid (N'-ethyl-N'-n-propylamine)amide, N-allyl-N-iso-propyl-3-aminopropionic acid iso-propylamine amide, N-allyl-N-iso-propyl-3-aminopropionic acid di-iso-propylamine amide, N-allyl-N-iso-propyl-3-aminopropionic acid (N'-methyl-N'-iso-propylamine)amide, N-allyl-N-iso-propyl-3-aminopropionic acid (N'-ethyl-N'-iso-propylamine)amide, N-allyl-N-iso-propyl-3-aminopropionic acid (N'-n-propyl-N'-iso-propylamine)amide, N-allyl-N-iso-propyl-3-aminopropionic acid allylamine amide, N-allyl-N-iso-propyl-3-aminopropionic acid diallylamine amide, N-allyl-N-iso-propyl-3-aminopropionic acid (N'-methyl-N'-allylamine)amide, N-allyl-N-iso-propyl-3-aminopropionic acid (N'-ethyl-N'-allylamine)amide, N-allyl-N-iso-propyl-3-aminopropionic acid (N'-n-propyl-N'-allylamine)amide, N-allyl-N-iso-propyl-3-aminopropionic acid (N'-iso-propyl-N'-allylamine)amide, N-allyl-N-iso-propyl-3-aminopropionic acid cyclohexylamine amide, N-allyl-N-iso-propyl-3-aminopropionic acid piperidine amide, N-allyl-N-iso-propyl-3-aminopropionic acid pyrrolidine amide, N-allyl-N-iso-propyl-3-aminopropionic acid hexamethyleneimine amide, and the like.

β-alanine amide and β-alanine methylamide are preferred because the effect of the present invention will be good.

β-alanine derivatives represented by general formula (3) according to the present invention will now be described.

In general formula (3), $R_5$ and $R_6$ are each independently a hydrogen atom, alkyl group with 1-7 carbons, alkenyl group with 1-7 carbons, hydrocarbon group with 3-7 carbons having a cyclic segment, pyridine group, cyclohexylcarbonyl group, cyclopentyl carbonyl group, nicotinoyl group, isonicotinoyl group, picolinoyl group, nipecotinoyl group, isonipecotinoyl group, N-acetyl nipecotinoyl group, N-acetyl isonipecotinoyl group, benzyloxycarbonyl group, a group represented by general formula (4)

[Chemical formula 14]

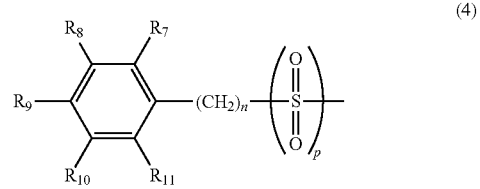

(4)

or a group represented by general formula (5)

[Chemical formula 15]

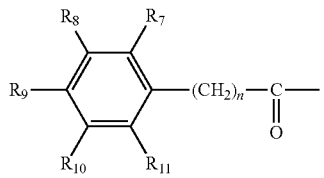

(5)

When one of $R_5$ and $R_6$ is a hydrogen atom, the other represents anything other than a hydrogen atom and $R_5$ and $R_6$ cannot both be hydrogen atoms.

Each group represented by $R_5$ and $R_6$ is described in detail below.

The alkyl group with 1-7 carbons is preferably an alkyl group with 1-3 carbons, such as a linear aliphatic chain or a branched aliphatic chain. Moreover, the alkenyl group with 1-7 carbons is preferably an alkenyl group with 1-3 carbons, such as a linear aliphatic chain or a branched aliphatic chain.

Examples of alkyl groups with 1-7 carbons and alkenyl groups with 1-7 carbons may include, for example, methyl group, ethyl group, n-propyl group, iso-propyl group, n-butyl group, iso-butyl group, ter-butyl group, 1-methylpropyl group, n-pentyl group, 1-methylbutyl group, 2-methylbutyl group, 3-methylbutyl group, 1,1-dimethylpropyl group, 2,2-dimethylpropyl group, 1,2-dimethylpropyl group, 1-ethylpropyl group, n-hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl, 2-ethylbutyl group, 1,1,2-trimethylpropyl group, 1,2,2-trimethylpropyl group, 1-ethyl-1-methyl-propyl group, 1-ethyl-2-methyl-propyl group, n-heptyl group, 1-methylhexyl group, 2-methylhexyl group, 3-methylhexyl group, 4-methylhexyl group, 5-methylhexyl group, 1,1-dimethylpentyl group, 1,2-dimethylpentyl group, 1,3-dimethylpentyl group, 1,4-dimethylpentyl group, 2,2-dimethylpentyl group, 2,3-dimethylpentyl group, 2,4-dimethylpentyl group, 3,3-dimethylpentyl group, 3,4-dimethylpentyl group, 4,4-dimethylpentyl group, 1-ethylpentyl group, 2-ethylpentyl group, 3-ethylpentyl group, 1,1,2-trimethylbutyl group, 1,1,3-trimethylbutyl group, 1,2,2-trimethylbutyl group, 1,2,3-trimethylbutyl group, 2,2,3-trimethylbutyl group, 2,3,3-trimethylbutyl group, 1-ethyl-1-methylbutyl group, 1-ethyl-2-methylbutyl group, 1-ethyl-3-methylbutyl group, 2-ethyl-methylbutyl group, 2-ethyl-2-methylbutyl group, 2-ethyl-3-methylbutyl group, 1-propylbutyl group, 1-ethyl-1,2-dimethylbutyl group, 1-ethyl-2,2-dimethylbutyl group, 1-propyl-2-methylpropyl group, 1-(1'-methylethyl)-2-methylbutyl group, 1,1,2,2-tetramethylpropyl group, allyl group, 1-methylallyl group, 2-butenyl group, 3-butenyl group, 3-methyl-2-butenyl group, 2-pentenyl group, 3-pentenyl group, 4-pentenyl group, 1,1-dimethylallyl group, 1-methyl-2-butenyl group, 1-methyl-3-butenyl group, 2-hexenyl group, 3-hexenyl group, 4-hexenyl group, 5-hexenyl group, 2,4-hexadienyl group, 4-methyl-3-pentenyl group, 2-heptenyl group, 3-heptenyl group, 4-heptenyl group, 5-heptenyl group, 6-heptenyl group, 2,4-heptadienyl group, 1-methyl-4-hexenyl group, 5-methyl-4-hexenyl group and the like.

The hydrocarbon group with 3-7 carbons having a cyclic segment can be any one of a cyclic aliphatic chain, an aliphatic chain having a cyclic segment, an unsaturated aliphatic chain, and the like.

Examples of hydrocarbon groups with 3-7 carbons having a cyclic segment may include, for example, cyclopropyl group, cyclopropylmethyl group, 1-methylcyclopropyl group, 2-methylcyclopropyl group, 3-methylcyclopropyl group, 1-cyclopropylethyl group, 2-cyclopropylethyl group, 1,2-dimethylcyclopropyl group, 2,2-dimethylcyclopropyl group, 2,3-dimethylcyclopropyl group, 1-cyclopropylpropyl group, 2-cyclopropylpropyl group, 3-cyclopropylpropyl group, (2'-methylcyclopropyl)methyl group, (2'-ethylcyclopropyl)methyl group, 1-ethylcyclopropyl group, 2-ethylcyclopropyl group, 1,2,3-trimethylcyclopropyl group, 2,2,3-trimethylcyclopropyl group, 1,2,2-trimethylcyclopropyl group, (1',2'-dimethylcyclopropyl)methyl group, (2'2'-dimethylcyclopropyl)methyl group, (2',3'-dimethylcyclopropyl)methyl group, 1-(1'-methylcyclopropyl)ethyl group, 1-(2'-methylcyclopropyl)ethyl group, 2-cyclopropylpropyl group, 2-(2'-methylcyclopropyl)ethyl group, 1-(1'-methylcyclopropyl)propyl group, 1-(2'-methylcyclopropyl)propyl group, 2-ethyl-1-methylcyclopropyl group, 2-ethyl-2-methylcyclopropyl group, 3-cyclopropylbutyl group, 2-cyclopropylbutyl group, 1-cyclopropylbutyl group, 2-cyclopropyl-1-methylethyl group, 3-(2'-methylcyclopropyl)propyl group, 1-(2'-propylcyclopropyl)methyl, 3-cyclopropyl-2-methylpropyl, 3-cyclopropyl-1-methylpropyl group, 3-cyclopropylpentyl group, 3-(2'-ethylcyclopropyl)ethyl group, 1,2-diethylcyclopropyl group, 2,2-diethylcyclopropyl group,
2-cyclopropyl-1-ethylethyl group, 2-(2',2'-dimethylcyclopropyl)ethyl group, 2-(2',3'-dimethylcyclopropyl)ethyl group, 2-(2',2'-dimethylcyclopropyl)butyl group, 2-(2',3'-dimethylcyclopropyl)butyl group, 2'-(2'-methylcyclopropyl)-1-methylethyl group, 2-cyclopropyl-1-methylbutyl group, tetramethylcyclopropyl group, (2',2',3'-trimethylcyclopropyl)methyl group, 1-(2',2'-dimethylcyclopropyl)ethyl group, 1-(2',3'-dimethylcyclopropyl)ethyl group, 1-(2',2'-dimethylcyclopropyl)-1-methylmethyl group, 1-(2',3'-dimethylcyclopropyl)-1-methylmethyl group, 1-(3'-methylcyclopropyl)-1-methylethyl group, 1-(2'-methylcyclopropyl)-1-methylethyl group, 1-(2'-ethylcyclopropyl)-1-methylmethyl group, 1-cyclopropyl-1-methylethyl group, cyclobutyl group, cyclobutylmethyl group, 1-methylcyclobutyl group, 2-methylcyclobutyl group, 3-methylcyclobutyl group, 1,2-dimethylcyclobutyl group, 1,3-dimethylcyclobutyl group, 2,2-dimethylcyclobutyl group, 2,3-dimethylcyclobutyl group, 2,4-dimethylcyclobutyl group, 3,3-dimethylcyclobutyl group, 1-ethylcyclobutyl group, 2-ethylcyclobutyl group, 3-ethylcyclobutyl group, 1-cyclobutylethyl group, 2-cyclobutylethyl group, 1-cyclobutyl-1-methylmethyl group, (2',2'-dimethylcyclobutyl)methyl group, (2',3'-dimethylcyclobutyl)methyl group, (3',3'-dimethylcyclobutyl)methyl group, (2',4'-dimethylcyclobutyl)methyl group, 1-(2'-methylcyclobutyl)ethyl group, 1-(3'-methylcyclobutyl)ethyl group, 1,2,2-trimethylcyclobutyl group, 1,2,3-trimethylcyclobutyl group, 1,3,3-trimethylcyclobutyl group, 1,2,4-trimethylcyclobutyl group, 2,2,3-trimethylcyclobutyl group, 2,3,3-trimethylcyclobutyl group, 2,3,4-trimethylcyclobutyl group, (2'-ethylcyclobutyl)methyl group, (3'-ethylcyclobutyl)methyl group, 1-cyclobutylpropyl group, 2-cyclobutylpropyl group, 3-cyclobutylpropyl group, 1-propylcyclobutyl group, 2-propylcyclobutyl group, 1-ethyl-2-methylcyclobutyl group, 2-ethyl-2-methylcyclobutyl group, 1-ethyl-3-methylcyclobutyl group, 3-ethyl-3-methylcyclobutyl group, 2-ethyl-3-methylcyclobutyl group, 3-ethyl-2-methylcyclobutyl group, 2-ethyl-1-methylcyclobutyl group, 3-ethyl-2-methylcyclobutyl group, 2-ethyl-4-methylcyclobutyl group, 4-ethyl-2-methylcyclobutyl group, 2-cyclobutyl-1-methylethyl group, 2-(2'-methylcyclobutyl)ethyl group, 2-(3'-methylcyclobutyl)ethyl group, cyclopentyl group, 1-methyl-2-propylcyclobutyl group, 1-methyl-3-propylcyclobutyl group, 2-methyl-2-propylcyclobutyl group, 3-methyl-3-propylcyclobutyl group, 2-methyl-3-propylcyclobutyl group, 2-methyl-1-propylcyclobutyl group, 3-methyl-1-propylcyclobutyl group, 2-methyl-4-propylcyclobutyl group, cyclopentyl group, cyclopentylmethyl group, (2'-methylcyclopentyl)methyl group, (3'-methylcyclopentyl)methyl group, 1-cyclopentylethyl group, 2-cyclopentylethyl group, 1,2-dimethylcyclopentyl group, 2,2-dimethylcyclopentyl group, 2,3-dimethylcyclopentyl group, 3,3-dimethylcyclopentyl group, 1,3-dimethylcyclopentyl group, 2,5-dimethylcyclopentyl group, 2,4-dimethylcyclopentyl group, 3,5-dimethylcyclopentyl group, 3,4-dimethylcyclopentyl group, 1-cyclopentyl-1-methylmethyl group, cyclohexyl group, cyclohexylmethyl group, 1-methylcyclohexyl group, 2-methylcyclohexyl group, 3-methylcyclohexyl group, cycloheptyl group, cyclopropylenyl group, cyclopropylenylmethyl group, cyclobutenyl group, cyclobutadienyl group, 1-cyclopentenyl group, 2-cyclopentenyl group, 3-cyclopentenyl group, cyclopentadienyl group, 2-methylcyclopentadienyl group, 3-methylcyclopentadienyl group, 2,2-dimethyl-1-cyclopentenyl group, 2,3-dimethyl-1-cyclopentenyl group, 2,4-dimethyl-1-cyclopentenyl group, 2,5-dimethyl-1-cyclopentenyl group, 3,3-dimethyl-1-cyclopentenyl group, 3,4-dimethyl-1-cyclopentenyl group, 3,5-dimethyl-1-cyclopentenyl group, 4,4-dimethyl-1-cyclopentenyl group, 4,5-dimethyl-1-cyclopentenyl group, 5,5-dimethyl-1-cyclopentenyl group, 1,2-dimethyl-2-cyclopentenyl group, 1,3-dimethyl-2-cyclopentenyl group, 1,4-dimethyl-2-cyclopentenyl group, 1,5-dimethyl-2-cyclopentenyl group, 2,3-dimethyl-2-cyclopentenyl group, 2,4-dimethyl-2-cyclopentenyl group, 2,5-dimethyl-2-cyclopentenyl group, dimethylcyclopentadienyl group, 3,4-dimethyl-2-cyclopentenyl group, 3,5-dimethyl-2-cyclopentenyl group, 4,4-dimethyl-2-cyclopentenyl group, 4,5-dimethyl-2-cyclopentenyl group, 5,5-dimethyl-2-cyclopentenyl group, cyclopentenylmethyl group, 1,2-dimethyl-3-cyclopentenyl group, 1,3-dimethyl-3-cyclopentenyl group, 2,2-dimethyl-3-cyclopentenyl group, 2,3-dimethyl-3-cyclopentenyl group, 2,4-dimethyl-3-cyclopentenyl group, 2,5-dimethyl-3-cyclopentenyl group, 3,4-dimethyl-3-cyclopentenyl group, 3,5-dimethyl-3-cyclopentenyl group, 1-(1'-cyclopentenyl)ethyl group, 1-(2'-cyclopentenyl)ethyl group, 1-(3'-cyclopentenyl)ethyl group, 2-(1'-cyclopentenyl)ethyl group, 2-(2'-cyclopentenyl)ethyl group, 2-(3'-cyclopentenyl)ethyl group, 1-cyclohexenyl group, 2-cyclohexenyl group, 3-cyclohexenyl group, 1,3-cyclohexadienyl group, 1,4-cyclohexadienyl group, 1,5-cyclohexadienyl group, 2,4-cyclohexadienyl group, 2,5-cyclohexadienyl group, 2-methyl-1-cyclohexenyl group, 3-methyl-1-cyclohexenyl group, 4-methyl-1-cyclohexenyl group, 5-methyl-1-cyclohexenyl group, 6-methyl-1-cyclohexenyl group, 1-methyl-2-cyclohexenyl group, 2-methyl-2-cyclohexenyl group, 3-methyl-2-cyclohexenyl group, 4-methyl-2-cyclohexenyl group, 5-methyl-2-cyclohexenyl group, 6-methyl-2-cyclohexenyl group, 1-methyl-3-cyclohexenyl group, 2-methyl-3-cyclohexenyl group, 3-methyl-3-cyclohexenyl group, 4-methyl-3-cyclohexenyl group, 5-methyl-3-cyclohexenyl group, 6-methyl-3-cyclohexenyl group, 1-cycloheptenyl group, 2-cycloheptenyl group, 3-cycloheptenyl group, 4-cycloheptenyl group, (1'-cyclohexenyl)methyl group, (2'-cyclohexenyl)methyl group, (3'-cyclohexenyl)methyl group, (1',3'-cyclohexadienyl)methyl group, (1',4'-cyclohexadienyl)methyl group, (1',5'-cyclohexadienyl)methyl group, (2',4'-cyclohexadienyl)methyl group, (2',5'-cyclohexadienyl)methyl group, and the like, but the present invention is not limited to these groups.

Cyclopropylmethyl group, 2-cyclopropylethyl group, 3-cyclopropylpropyl group, 4-cyclopropylbutyl group, cyclobutyl group, cyclobutylmethyl group, 2-cyclobutylethyl group, 3-cyclobutylpropyl group, cyclopentyl group, cyclopentylmethyl group, 2-cyclopentylethyl group, cyclohexyl group, cyclohexylmethyl group, methylcyclohexyl group, cycloheptyl group, cyclohexenyl group, cyclohexadienyl group, and the like are preferred because the synthesis in the present invention will become easy. Hydrocarbon groups having a cyclohexyl segment are the most preferred because the effect of the present invention will be good. Examples may include, for example, cyclohexyl group, cyclohexylmethyl group, methylcyclohexyl group, cyclohexenyl group, cyclohexadienyl group, and the like.

In the general formula (4), p represents an integer of 0 or 1. When p is 0, the compound of the present invention is an N-allyl-β-alanine or N-aralkyl-β-alanine corresponding to $R_7$-$R_{11}$ and n. When p is 1, the compound of the present invention is an N-sulfonyl-β-alanine derivative corresponding to $R_7$-$R_{11}$ and n.

In the general formula (4), n represents an integer of 0, 1, or 2. In cases in which p is 0: WHEN N IS 0, the compound of the present invention is an N-phenyl-β-alanine derivative corresponding to $R_7$ through $R_{11}$; when n is 1, the compound of the present invention is an N-benzyl-β-alanine derivative corresponding to $R_7$ through $R_{11}$; and when n is 2, the compound of the present invention is an N-phenylethyl-β-alanine derivative corresponding to $R_7$ through $R_{11}$. In cases in which p is 1: when n is 0, the compound of the present invention is an N-benzenesulfonyl-β-alanine derivative corresponding to $R_7$ through $R_{11}$; when n is 1, the compound of the present invention is an N-benzylsulfonyl-β-alanine derivative corresponding to $R_7$ through $R_{11}$; and when n is 2, the compound of the present invention is an N-phenylethylsulfonyl-β-alanine derivative corresponding to $R_7$ through $R_{11}$.

Moreover, in general formula (4), $R_7$ through $R_{11}$ each independently represents a hydrogen atom, hydroxyl group, alkyloxy group with 1-4 carbons, alkenyloxy group with 1-4 carbons, alkyl group with 1-3 carbons, or alkenyl group with 1-3 carbons. When the number of carbons in the alkyloxy and alkenyloxy groups exceeds 4, the solubility of the same in a Preparation Example becomes poor and the molecular weight increases at the same time, whereby the effect of the present invention becomes poor. Any alkyloxy or alkenyloxy group can be used as long as the hydrocarbon segment is a segment with 1-4 carbons, and examples may include, for example, methyl, ethyl, n-propyl, iso-propyl, n-butyl, iso-butyl, tert-butyl, 1-methylpropyl, allyl(2-propenyl), 2-butenyl, 3-butenyl, 1-methyl-2-propenyl, 2-methyl-2-propenyl, cyclopropyl, cyclobutyl, cyclopropylmethyl, cyclopropenyl, cyclopropenylmethyl, and cyclobutenyl groups.

When the number of carbons in the alkyl or alkenyl group exceeds 3, the solubility in a Preparation Example becomes poor and the molecular weight increases at the same time, whereby the effect of the present invention will become poor. Any alkyl or alkenyl group can be used as long as the hydrocarbon segment is a segment with 1-3 carbons. Examples may include, for example, methyl group, ethyl group, n-propyl group, iso-propyl group, allyl(2-propenyl) group, cyclopropyl group, and cyclopropenyl groups. However, the present invention is not limited to these examples.

Examples of groups represented by general formula (4) may include, for example, phenyl group, 4-methoxyphenyl group, 3-methoxyphenyl group, 2-methoxyphenyl group, 4-ethoxyphenyl group, 3-ethoxyphenyl group, 2-ethoxyphenyl group, 4-propoxyphenyl group, 3-propoxyphenyl group, 2-propoxyphenyl group, 4-butoxyphenyl group, 3-butoxyphenyl group, 2-butoxyphenyl group, 2,4-dimethoxyphenyl group, 3,4-dimethoxyphenyl group, 3,4,5-trimethoxyphenyl group, 2-hydroxyphenyl group, 3-hydroxyphenyl group, 4-hydroxyphenyl group, 2,4-dihydroxyphenyl group, 3,4-dihydroxyphenyl group, 3,4,5-trihydroxyphenyl group, 2-hydroxy-4-methoxyphenyl group, 3-hydroxy-4-methoxyphenyl group, 4-hydroxy-3-methoxyphenyl group, 2-methylphenyl group, 3-methylphenyl group, 4-methylphenyl group, 2-ethylphenyl group, 3-ethylphenyl group, 4-ethylphenyl group, 2-propylphenyl group, 3-propylphenyl group, 4-propylphenyl group, benzyl group, 4-methoxybenzyl group, 3-methoxybenzyl group, 2-methoxybenzyl group, 4-ethoxybenzyl group, 3-ethoxybenzyl group, 2-ethoxybenzyl group, 4-propoxybenzyl group, 3-propoxybenzyl group, 2-propoxybenzyl group, 4-butoxybenzyl group, 3-butoxybenzyl group, 2-butoxybenzyl group, 2,4-dimethoxybenzyl group, 3,4-dimethoxybenzyl group, 3,4,5-trimethoxybenzyl group, 2-hydroxybenzyl group, 3-hydroxybenzyl group, 4-hydroxybenzyl group, 2,4-dihydroxybenzyl group, 3,4-dihydroxybenzyl group, 3,4,5-trihydroxybenzyl group, 2-hydroxy-4-methoxybenzyl group, 3-hydroxy-4-methoxybenzyl group, 4-hydroxy-3-methoxybenzyl group, 2-methylbenzyl group, 3-methylbenzyl group, 4-methylbenzyl group, 2-ethylbenzyl group, 3-ethylbenzyl group, 4-ethylbenzyl group, 2-propylbenzyl group, 3-propylbenzyl group, 4-propylbenzyl group, phenylethyl group, 4-methoxyphenylethyl group, 3-methoxyphenylethyl group, 2-methoxyphenylethyl group, 4-ethoxyphenylethyl group, 3-ethoxyphenylethyl group, 2-ethoxyphenylethyl group, 4-propoxyphenylethyl group, 3-propoxyphenylethyl group, 2-propoxyphenylethyl group, 4-butoxyphenylethyl group, 3-butoxyphenylethyl group, 2-butoxyphenylethyl group, 2,4-dimethoxyphenylethyl group, 3,4-dimethoxyphenylethyl group, 3,4,5-trimethoxyphenylethyl group, 2-hydroxyphenylethyl group, 3-hydroxyphenylethyl group, 4-hydroxyphenylethyl group, 2,4-dihydroxyphenylethyl group, 3,4-dihydroxyphenylethyl group, 3,4,5-trihydroxyphenylethyl group, 2-hydroxy-4-methoxyphenylethyl group, 3-hydroxy-4-methoxyphenylethyl group, 4-hydroxy-3-methoxyphenylethyl group, 2-methylphenylethyl group, 3-methylphenylethyl group, 4-methylphenylethyl group, 2-ethylphenylethyl group, 3-ethylphenylethyl group, 4-ethylphenylethyl group, 2-propylphenylethyl group, 3-propylphenylethyl group, 4-propylphenylethyl group, benzenesulfonyl group, 2-methoxybenzenesulfonyl group, 3-methoxybenzenesulfonyl group, 4-methoxybenzenesulfonyl group, 4-ethoxybenzenesulfonyl group, 3-ethoxybenzenesulfonyl group, 2-ethoxybenzenesulfonyl group, 4-propoxybenzenesulfonyl group, 3-propoxybenzenesulfonyl group, 2-propoxybenzenesulfonyl group, 4-butoxybenzenesulfonyl group, 3-butoxybenzenesulfonyl group, 2-butoxybenzenesulfonyl group, 2,4-dimethoxybenzenesulfonyl group, 3,4-dimethoxybenzenesulfonyl group, 3,4,5-trimethoxybenzenesulfonyl group, 2-hydroxybenzenesulfonyl group, 3-hydroxybenzenesulfonyl group, 4-hydroxybenzenesulfonyl group, 2,4-dihydroxybenzenesulfonyl group, 3,4-dihydroxybenzenesulfonyl group, 3,4,5-trihydroxybenzenesulfonyl group, 2-hydroxy-4-methoxybenzenesulfonyl group, 3-hydroxy-4-methoxybenzenesulfonyl group, 4-hydroxy-3-methoxybenzenesulfonyl group, 2-methylbenzenesulfonyl group, 3-methylbenzenesulfonyl group, 4-methylbenzenesulfonyl group, 2-ethylbenzenesulfonyl group, 3-ethylbenzenesulfonyl group, 4-ethylbenzenesulfonyl group, 2-propylbenzenesulfonyl group, 3-propylbenzenesulfonyl group, 4-propylbenzenesulfonyl group, benzylsulfonyl group, 2-methoxybenzylsulfonyl group, 3-methoxybenzylsulfonyl group, 4-methoxybenzylsulfonyl group, 4-ethoxybenzylsulfonyl group, 3-ethoxybenzylsulfonyl group, 2-ethoxybenzylsulfonyl group, 4-propoxybenzylsulfonyl group, 3-propoxybenzylsulfonyl group, 2-propoxybenzylsulfonyl group, 4-butoxybenzylsulfonyl group, 3-butoxybenzylsulfonyl group, 2-butoxybenzylsulfonyl group, 2,4-dimethoxybenzylsulfonyl group, 3,4-dimethoxybenzylsulfonyl group, 3,4,5-trimethoxybenzylsulfonyl group, 2-hydroxybenzylsulfonyl group, 3-hydroxybenzylsulfonyl group, 4-hydroxybenzylsulfonyl group, 2,4-dihydroxybenzylsulfonyl group, 3,4-dihydroxybenzylsulfonyl group, 3,4,5-trihydroxybenzylsulfonyl group, 2-hydroxy-4-methoxybenzylsulfonyl group, 3-hydroxy-4-methoxybenzylsulfonyl group, 4-hydroxy-3-methoxybenzylsulfonyl group, 2-methylbenzylsulfonyl group, 3-methylbenzylsulfonyl group, 4-methylbenzylsulfonyl group, 2-ethylbenzylsulfonyl group, 3-ethylbenzylsulfonyl group, 4-ethylbenzylsulfonyl group, 2-propylbenzylsulfonyl group, 3-propylbenzylsulfonyl group, 4-propylbenzylsulfonyl group, phenylethylsulfonyl group, 4-methoxyphenylethylsulfonyl group, 3-methoxyphenylethylsulfonyl group, 2-methoxyphenylethylsulfonyl group, 4-ethoxyphenylethylsulfonyl group, 3-ethoxyphenylethylsulfonyl group, 2-ethoxyphenylethylsulfonyl group, 4-propoxyphenylethylsulfonyl group, 3-propoxyphenylethylsulfonyl group, 2-propoxyphenylethylsulfonyl group, 4-butoxyphenylethylsulfonyl group, 3-butoxyphenylethylsulfonyl group, 2-butoxyphenylethylsulfonyl group, 2,4-dimethoxyphenylethylsulfonyl group, 3,4-dimethoxyphenylethylsulfonyl group, 3,4,5-trimethoxyphenylethylsulfonyl group, 2-hydroxyphenylethylsulfonyl group, 3-hydroxyphenylethylsulfonyl group, 4-hydroxyphenylethylsulfonyl group, 2,4-dihydroxyphenylethylsulfonyl group, 3,4-dihydroxyphenylethylsulfonyl group, 3,4,5-trihydroxyphenylethylsulfonyl group, 2-hydroxy-4-methoxyphenylethylsulfonyl group, 3-hydroxy-4-methoxyphenylethylsulfonyl group, 4-hydroxy-3-methoxyphenylethylsulfonyl group, 2-methylphenylethylsulfonyl group, 3-methylphenylethylsulfonyl group, 4-methylphenylethylsulfonyl group, 2-ethylphenylethylsulfonyl group, 3-ethylphethylthylsulfonyl group, 4-ethylphenylethylsulfonyl group, 2-propylphenylethylsulfonyl group, 3-propylphenylethylsulfonyl group, 4-propylphenylethylsulfonyl groups, and the like.

In terms of ease of compound synthesis, it is preferred that $R_7$ through $R_{11}$ in the general formula (4) each independently be a hydrogen, hydroxyl group, or alkyloxy group with 1-4 carbons. It is preferred that each of $R_7$ through $R_{11}$ be a hydrogen atom, or that one or more of $R_7$ through $R_{11}$ be alkyloxy group with 1-4 carbons because the effect of the present invention will be good. It is preferred that the alkyloxy group with 1-4 carbons be a methoxy group because the solubility and effect will be good. It is particularly preferred that each of $R_7$ through $R_{11}$ be a hydrogen atom because the solubility and effect will both be the best.

In the general formula (5), n represents an integer of 0, 1, or 2, as in general formula (4). When n is 0, the compound of the present invention is an N-benzoyl-β-alanine derivative corresponding to $R_7$ through $R_{11}$. When n is 1, the compound of the present invention is an N-phenylacetyl-β-alanine derivative corresponding to $R_7$ through $R_{11}$, and when n is 2, the compound of the present invention is an N-phenylpropionyl-β-alanine derivative corresponding to $R_7$ through $R_{11}$.

Moreover, in general formula (5), $R_7$ through $R_{11}$ each independently represents a hydrogen atom, hydroxyl group, alkyloxy group with 1-4 carbons, alkenyloxy group with 1-4 carbons, alkyl group with 1-3 carbons, or alkenyl group with 1-3 carbons. When the number of carbons in the alkyloxy or alkenyloxy group exceeds 4, the effect of the present invention is inferior because the solubility in a Preparation Example becomes poor and the molecular weight increases at the same time. Any alkyloxy or alkenyloxy group can be used as long as the hydrocarbon segment is a segment with 1-4 carbons, and specific examples may include, for example, methyl, ethyl, n-propyl, iso-propyl, n-butyl, iso-butyl, tert-butyl, 1-methylpropyl, allyl(2-propenyl), 2-butenyl, 3-butenyl, 1-methyl-2-propenyl, 2-methyl-2-propenyl, cyclopropyl, cyclobutyl, cyclopropylmethyl, cyclopropenyl, cyclopropenylmethyl, and cyclobutenyl groups.

When the number of carbons in the alkyl or alkenyl group exceeds 3, the effect of the present invention will be inferior because the solubility in a Preparation Example becomes poor and the molecular weight increases at the same time. Any alkyl or alkenyl group can be used as long as the hydrocarbon segment is a segment with 1-3 carbons. Examples may include, for example, methyl, ethyl, n-propyl, iso-propyl, allyl(2-propenyl), cyclopropyl, and cyclopropenyl groups.

Examples of groups represented by general formula (5) may include, for example, benzoyl group, p-anisoyl(4-methoxybenzoyl) group, m-anisoyl(3-methoxybenzoyl) group, o-anisoyl(2-methoxybenzoyl) group, 4-ethoxybenzoyl group, 3-ethoxybenzoyl group, 2-ethoxybenzoyl group, 4-propoxybenzoyl group, 3-propoxybenzoyl group, 2-propoxybenzoyl group, 4-butoxybenzoyl group, 3-butoxybenzoyl group, 2-butoxybenzoyl group, 2,4-dimethoxybenzoyl group, 3,4-dimethoxybenzoyl group, 3,4,5-trimethoxybenzoyl group, 2,3,4-trimethoxybenzoyl group, 2-hydroxybenzoyl(salicyl) group, 3-hydroxybenzoyl group, 4-hydroxybenzoyl group, N-2,4-dihydroxybenzoyl group, N-3,4-dihydroxybenzoyl group, N-3,4,5-trihydroxybenzoyl (galloyl) group, 2-hydroxy-4-methoxybenzoyl group, 3-hydroxy-4-methoxybenzoyl group, 4-hydroxy-3-methoxybenzoyl group, 2-methylbenzoyl (o-toluoyl) group, 3-methylbenzoyl (m-toluoyl) group, 4-methylbenzoyl (p-toluoyl) group, 2-ethylbenzoyl group, 3-ethylbenzoyl group, 4-ethylbenzoyl group, 2-propylbenzoyl group, 3-propylbenzoyl group, 4-propylbenzoyl group, phenylacetyl group, 4-methoxyphenylacetyl group, 3-methoxyphenylacetyl group, 2-methoxyphenylacetyl group, 4-ethoxyphenylacetyl group, 3-ethoxyphenylacetyl group, 2-ethoxyphenylacetyl group, 4-propoxyphenylacetyl group, 3-propoxyphenylacetyl group, 2-propoxyphenylacetyl group, 4-butoxyphenylacetyl group, 3-butoxyphenylacetyl group, 2-butoxyphenylacetyl group, 2,4-dimethoxyphenylacetyl group, 3,4-dimethoxyphenylacetyl group, 3,4,5-trimethoxyphenylacetyl group, 2-hydroxyphenylacetyl group, 3-hydroxyphenylacetyl group, 4-hydroxyphenylacetyl group, N-2,4-dihydroxyphenylacetyl group, N-3,4-dihydroxyphenylacetyl group, N-3,4,5-trihydroxyphenylacetyl group, 2-hydroxy-4-methoxyphenylacetyl group, 3-hydroxy-4-methoxyphenylacetyl group, 4-hydroxy-3-methoxyphenylacetyl group, 2-methylphenylacetyl group, 3-methylphenylacetyl group, 4-methylphenylacetyl group, 2-ethylphenylacetyl group, 3-ethylphenylacetyl group, 4-ethylphenylacetyl group, 2-propylphenylacetyl group, 3-propylphenylacetyl group, 4-propylphenylacetyl group, phenylpropionyl group, 4-methoxyphenylpropionyl group, 3-methoxyphenylpropionyl group, 2-methoxyphenylpropionyl group, 4-ethoxyphenylpropionyl group, 3-ethoxyphenylpropionyl group, 2-ethoxyphenylpropionyl group, 4-propoxyphenylpropionyl group, 3-propoxyphenylpropionyl group, 2-propoxyphenylpropionyl group, 4-butoxyphenylpropionyl group, 3-butoxyphenylpropionyl group, 2-butoxyphenylpropionyl group, 2,4-dimethoxyphenylpropionyl group, 3,4-dimethoxyphenylpropionyl group, 3,4,5-trimethoxyphenylpropionyl group, 2-hydroxyphenylpropionyl group, 3-hydroxyphenylpropionyl group, 4-hydroxyphenylpropionyl group, N-2,4-dihydroxyphenylpropionyl group, N-3,4-dihydroxyphenylpropionyl group, N-3,4,5-trihydroxyphenylpropionyl group, 2-hydroxy-4-methoxyphenylpropionyl group, 3-hydroxy-4-methoxyphenylpropionyl group, 4-hydroxy-3-methoxyphenylpropionyl group, 2-methylphenylpropionyl group, 3-methylphenylpropionyl group, 4-methylphenylpropionyl group, 2-ethylphenylpropionyl group, 3-ethylphenylpropionyl group, 4-ethylphenylpropionyl group, 2-propylphenylpropionyl group, 3-propylphenylpropionyl group, 4-propylphenylpropionyl group, and the like.

In terms of ease of compound synthesis, it is preferred that $R_7$ through $R_{11}$ in the general formula (5) each independently be a hydrogen, hydroxyl group, or alkyloxy group with 1-4 carbons. It is preferred that each of $R_7$ through $R_{11}$ be a hydrogen atom, or that one or more of $R_7$ through $R_{11}$ be an alkyloxy group with 1-4 carbons because the effect of the present invention will become good. It is preferred that the alkyloxy group with 1-4 carbons be a methoxy group because the solubility and effect invention will be good. It is particularly preferred that each of $R_7$ through $R_{11}$ be a hydrogen atom because the solubility and effect will both be the best.

It is preferred that one of $R_5$ and $R_6$ in the β-alanine derivative represented by general formula (3) of the present invention be a hydrogen atom or an alkyl group with 1-3 carbons because the effect of the present invention will be good. Examples of alkyl groups with 1-3 carbons may include, for example, methyl group, ethyl group, n-propyl group, iso-propyl group, and the like. Of these, a methyl group is preferred. It is further preferred that one of $R_5$ and $R_6$ be a hydrogen atom. As described above, $R_5$ and $R_6$ cannot both be a hydrogen atom at the same time.

When one of the $R_5$ and $R_6$ in the β-alanine derivative represented by general formula (3) of the present invention is an alkyl group with 1-7 carbons or an alkenyl group with 1-7 carbons, (the other) one is preferably an alkyl group with 1-3 carbons, alkenyl group with 1-3 carbons, or hydrogen atom because the effect of the present invention will be good. It is more preferable that (the other) one be a hydrogen atom. It is further preferred that one of $R_5$ and $R_6$ be an alkyl group with 1-3 carbons or an alkenyl group with 1-3 carbons and that (the other) one be a hydrogen atom. It is particularly preferred that one of $R_5$ and $R_6$ be an alkyl group with 1-3 carbons and that (the other) one be a hydrogen atom.

Examples of the corresponding β-alanine derivative may include, for example, N-monomethyl-β-alanine (N-methyl-β-alanine), N-monoethyl-β-alanine, N-mono-n-propyl-β-alanine, N-mono-iso-propyl-β-alanine, and N-monoallyl-β-alanine. Although these compounds are preferred because the effect of the present invention will be good, the present invention is not limited to these examples.

When one of $R_5$ and $R_6$ in the β-alanine derivative represented by general formula (3) of the present invention is a hydrocarbon group with 3-7 carbons having a cyclic segment, (the other) one is preferably a hydrogen atom, alkyl group with 1-3 carbons, or alkenyl group with 1-3 carbons because the effect of the present invention will be good. A hydrogen atom or alkyl group with 1-3 carbons is more preferable, and a hydrogen atom is further preferred. The preferred structure of the present invention is such that one of $R_5$ and $R_6$ is a hydrocarbon group with 3-7 carbons having a ring segment and (the other) one is a hydrogen atom or methyl group. It is particularly preferred that one of $R_5$ and $R_6$ be a hydrocarbon group having a cyclohexyl segment and (the other) one be a hydrogen atom or methyl group.

Examples of the corresponding β-alanine derivative may include, for example, N-cyclohexyl-β-alanine, N-cyclohexylmethyl-β-alanine, and N-methylcyclohexyl-β-alanine, as well as these β-alanine derivatives where the amino group of the β-alanine segment is N-methylated, N-ethylated, N-propylated, N-allylated form, or the like. Although these compounds are preferred because the effect of the present invention will be good, the present invention is not limited to these examples.

In terms of ease of compound synthesis, in cases in which one of $R_5$ and $R_6$ in the β-alanine derivative represented by formula (3) of the present invention is a pyridyl group, it is preferred that (the other) one be a hydrogen atom, alkyl group with 1-7 carbons, alkenyl group with 1-7 carbons, or hydrocarbon group with 3-7 carbons having a cyclic segment. It is further preferred that (the other) one be a hydrogen atom, alkyl group with 1-3 carbons, or alkenyl group with 1-3 carbons because the effect of the present invention will be good; and a hydrogen atom is most preferable.

Examples of the corresponding β-alanine derivative may include, for example, N-(2'-pyridyl)-β-alanine, N-(3'-pyridyl)-β-alanine, and N-(4'-pyridyl)-β-alanine, as well as these β-alanine derivatives in which the amino group of the β-alanine segment is N-methylated, N-ethylated, N-propylated, or N-allylated form, or the like. Although these compounds are preferred because the effect of the present invention will be good, the present invention is not limited to these examples.

When one of the $R_5$ and $R_6$ in the β-alanine derivative shown in the general formula (3) according to the present invention is a cyclohexylcarbonyl group, cyclopentyl carbonyl group, nicotinoyl group, isonicotinoyl group, picolinoyl group, nipecotinoyl group, isonipecotinoyl group, N-acetyl nipecotinoyl group, N-acetyl isonipecotinoyl group, or benzyloxycarbonyl group, in terms of ease of compound synthesis, it is preferred that (the other) one be a hydrogen atom, pyridyl group, alkyl group with 1-7 carbons, alkenyl group with 1-7 carbons, or hydrocarbon group with 3-7 carbons having a cyclic segment, or any of the groups shown in the general formula (4). A hydrogen atom, pyridyl group, alkyl group with 1-7 carbons, alkenyl group with 1-7 carbons, or hydrocarbon group with 3-7 carbons having a cyclic segment is further preferred. It is further preferred that (the other) one be a hydrogen atom, alkyl group with 1-3 carbons, or alkenyl group with 1-3 carbons because the effect of the present invention will be good; and a hydrogen atom is most preferable.

Examples of the corresponding β-alanine derivatives may include, for example, N-cyclohexylcarbonyl-β-alanine (N-hexahydrobenzoyl-β-alanine), N-cyclopentylcarbonyl-β-alanine, N-nicotinoyl-β-alanine, N-iso-nicotinoyl-β-alanine, N-picolinoyl-β-alanine, N-nipecotinoyl-β-alanine, N-isonipecotinoyl-β-alanine, N—(N'-acetylnicotinoyl)-β-alanine, N—(N'-acetyl nipecotinoyl)-β-alanine, N—(N'-acetyl-isonipecotinoyl)-β-alanine, and N-benzyloxycarbonyl-β-alanine, as well as β-alanine derivatives in which the amino group of the β-alanine segment is N-methylated, N-ethylated, N-propylated, or N-allylated form, or the like. Although these compounds are preferred because the effect of the present invention will be good, the present invention is not limited to these examples.

Moreover, when one of the $R_5$ and $R_6$ in the β-alanine derivative represented by the general formula (3) according to the present invention is a group represented by general formula (4), in terms of ease of synthesis, it is preferred that (the other) one is a hydrogen atom, alkyl group with 1-7 carbons, alkenyl group with 1-7 carbons, a hydrocarbon group with 3-7 carbons having a cyclic segment, or a group represented by general formula (4). A hydrogen atom, alkyl group with 1-3 carbons, or alkenyl group with 1-3 carbons is further preferred because the effect of the present invention and the solubility will be good. A hydrogen atom is most preferable.

Examples of corresponding β-alanine derivatives may include, for example, N-phenyl-β-alanine, N-4'-methoxyphenyl-β-alanine, N-3'-methoxyphenyl-β-alanine, N-2'-methoxyphenyl-β-alanine, N-4'-ethoxyphenyl-β-alanine, N-3'-ethoxyphenyl-β-alanine, N-2'-ethoxyphenyl-β-alanine, N-4'-propoxyphenyl-β-alanine, N-3'-propoxyphenyl-β-alanine, N-2'-propoxyphenyl-(β-alanine, N-4'-butoxyphenyl-β-alanine, N-3'-butoxyphenyl-β-alanine, N-2'-butoxyphenyl-β-alanine, N-2',4'-dimethoxyphenyl-β-alanine, N-3',4'-dimethoxyphenyl-β-alanine, N-3',4',5'-trimethoxyphenyl-β-alanine, N-2'-hydroxyphenyl-β-alanine, N-3'-hydroxyphenyl-β-alanine, N-4'-hydroxyphenyl-β-alanine, N-2',4'-dihydroxyphenyl-(β-alanine, N-3',4'-dihydroxyphenyl-β-alanine, N-3',4',5'-trihydroxyphenyl-β-alanine, N-2'-hydroxy-4'-methoxyphenyl-β-alanine, N-(2'-hydroxy-4'-methoxyphenyl)-β-alanine, N-(3'-hydroxy-4'-methoxyphenyl)-β-alanine, N-(4'-hydroxy-3'-methoxyphenyl)-β-alanine, N-2'-methylphenyl-β-alanine, N-3'-methylphenyl-β-alanine, N-4'-methylphenyl-β-alanine, N-2'-ethylphenyl-β-alanine, N-3'-ethylphenyl-β-alanine, N-4'-ethylphenyl-β-alanine, N-2'-propylphenyl-β-alanine, N-3'-propyl phenyl-β-alanine, N-4'-propyl phenyl-β-alanine, N-benzyl-β-alanine, N-4'-methoxybenzyl-β-alanine, N-3'-methoxybenzyl-β-alanine, N-2'-methoxybenzyl-β-alanine, N-4'-ethoxybenzyl-β-alanine, N-3'-ethoxybenzyl-β-alanine, N-2'-ethoxybenzyl-Jβ-alanine, N-4'-propoxybenzyl-β-alanine, N-3'-propoxybenzyl-β-alanine, N-2'-propoxybenzyl-β-alanine, N-4'-butoxybenzyl-β-alanine, N-3'-butoxybenzyl-β-alanine, N-2'-butoxybenzyl-(β-alanine, N-2',4'-dimethoxybenzyl-β-alanine, N-3',4'-dimethoxybenzyl-β-alanine, N-3',4',5'-trimethoxybenzyl-β-alanine, N-2'-hydroxybenzyl-β-alanine, N-3'-hydroxybenzyl-β-alanine, N-4'-hydroxybenzyl-β-alanine, N-2',4'-dihydroxybenzyl-β-alanine, N-3',4'-dihydroxybenzyl-β-alanine, N-3',4',5'-trihydroxybenzyl-β-alanine, N-(2'-hydroxy-4'-methoxybenzyl)-β-alanine, N-(3'-hydroxy-4'-methoxybenzyl)-β-alanine, N-(4'-hydroxy-3'-methoxybenzyl)-β-alanine, N-2'-methylbenzyl-β-alanine, N-3'-methylbenzyl-β-alanine, N-4'-methylbenzyl-β-alanine, N-2'-ethylbenzyl-β-alanine, N-3'-ethylbenzyl-β-alanine, N-4'-ethyl benzyl-β-alanine, N-2'-propylbenzyl-β-alanine, N-3'-propylbenzyl-β-alanine, N-4'-propylbenzyl-Jβ-alanine, N-phenylethyl-β-alanine, N-4'-methoxyphenylethyl-β-alanine, N-3'-methoxyphenylethyl-β-alanine, N-2'-methoxyphenylethyl-β-alanine, N-4'-ethoxyphenylethyl-β-alanine, N-3'-ethoxyphenylethyl-β-alanine, N-2'-ethoxyphenylethyl-β-alanine, N-4'-propoxyphenylethyl-β-alanine, N-3'-propoxyphenyethyl-β-alanine, N-2'-propoxyphenylethyl-β-alanine, N-4'-butoxyphenylethyl-β-alanine, N-3'-butoxyphenyethyl-β-alanine, N-2'-butoxyphenylethyl-β-alanine, N-2',4'-dimethoxyphenylethyl-β-alanine, N-3',4'-dimethoxyphenyethyl-β-alanine, N-3',4',5'-trimethoxyphenylethyl-β-alanine, N-2'-hydroxyphenylethyl-(β-alanine, N-3'-hydroxyphenyethyl-β-alanine, N-4'-hydroxyphenylethyl-β-alanine, N-2',4'-dihydroxyphenylethyl-β-alanine, N-3',4'-dihydroxyphenylethyl-(β-alanine, N-3',4',5'-trihydroxyphenylethyl-Jβ-alanine, N-(2'-hydroxy-4'- methoxyphenylethyl)-β-alanine, N-(3'-hydroxy-4'-methoxyphenylethyl)-β-alanine, N-(4'-hydroxy-3'-methoxyphenylethy)-β-alanine, N-2'-methylphenylethyl-β-alanine, N-3'-methylphenyl ethyl-β-alanine, N-4'-methylphenylethyl-β-alanine, N-2'-ethylphenylethyl-β-alanine, N-3'-ethyl phenylethyl-β-alanine, N-4'-ethylphenylethyl-O-alanine, N-2'-propylphenylethyl-β-alanine, N-3'-propylphenylethyl-β-alanine, N-4'-propylphenylethyl-β-alanine, N-benzenesulfonyl-β-alanine, N-4'-methoxybenzenesulfonyl-β-alanine, N-3'-methoxybenzenesulfonyl-β-alanine, N-2'-methoxybenzenesulfonyl-β-alanine, N-benzylsulfonyl-β-alanine, N-4'-methoxybenzylsulfonyl-β-alanine, N-3'-methoxybenzylsulfonyl-β-alanine, N-2'-methoxybenzylsulfonyl-β-alanine, N-phenylethyl sulfonyl-β-alanine, N-4'-methoxyphenylethylsulfonyl-β-alanine, N-3'-methoxyphenylethylsulfonyl-β-alanine, and N-2'-methoxyphenylethylsulfonyl-β-alanine, as well as β-alanine derivatives in which the amino group of the β-alanine segment is N-methylated, N-ethylated, N-propylated, or N-allylated form, or the like. However, the present invention is not limited to these examples.

It is most preferred that the β-alanine derivative represented by general formula (3) according to the present invention be a β-alanine derivative in which, when one of $R_5$ and $R_6$ is a group represented by the general formula (4), each of $R_7$ through $R_{11}$ is a hydrogen atom, or one or more of $R_7$ through $R_{11}$ is an alkyloxy group with 1-4 carbons, and the (other) ones are hydrogen atoms. Examples may include, for example, N-phenyl-β-alanine, N-4'-methoxyphenyl-β-alanine, N-3'-methoxyphenyl-β-alanine, N-2'-methoxyphenyl-β-alanine, N-benzyl-β-alanine, N-4'-methoxybenzyl-β-alanine, N-3'-methoxybenzyl-β-alanine, N-2'-methoxybenzyl-β-alanine, N-phenylethyl-β-alanine, N-4'-methoxyphenylethyl-β-alanine, N-3'-methoxyphenylethyl-β-alanine, N-2'-methoxyphenylethyl-β-alanine, N-benzenesulfonyl-β-alanine, N-4'-methoxybenzenesulfonyl-β-alanine, N-3'-methoxybenzenesulfonyl-β-alanine, N-2'-methoxybenzenesulfonyl-β-alanine, N-benzylsulfonyl-β-alanine, N-4'-methoxybenzylsulfonyl-β-alanine, N-3'-methoxybenzylsulfonyl-β-alanine, N-2'-methoxybenzylsulfonyl-β-alanine, N-phenylethylsulfonyl-β-alanine, N-4'-methoxyphenylethylsulfonyl-β-alanine, N-3'-methoxyphenylethylsulfonyl-β-alanine, and N-2'-methoxyphenylethylsulfonyl-β-alanine.

Moreover, when one of the $R_5$ and $R_6$ in the β-alanine derivative shown in the general formula (3) according to the present invention is a group represented by general formula (5), in terms of ease of synthesis, it is preferred that (the other) one is a hydrogen atom, an alkyl group with 1-7 carbons, an alkenyl group with 1-7 carbons, a pyridyl group, a hydrocarbon group with 3-7 carbons having a cyclic segment, or a group represented by general formula (4). A hydrogen atom, alkyl group with 1-3 carbons, or alkenyl group with 1-3 carbons is further preferred because the effect of the present invention and the solubility will be good. A hydrogen atom is most preferable.

Examples of corresponding β-alanine derivatives may include, for example, N-benzoyl-β-alanine, N-p-anisoyl-β-alanine (N-4'-methoxybenzoyl-β-alanine), N-m-anisoyl-β-alanine (N-3'-methoxybenzoyl-β-alanine), N-o-anisoyl-β-alanine (N-2'-methoxybenzoyl-β-alanine), N-4'-ethoxybenzoyl-β-alanine, N-3'-ethoxybenzoyl-β-alanine, N-2'-ethoxybenzoyl-β-alanine, N-4'-propoxybenzoyl-β-alanine, N-3'-propoxybenzoyl-β-alanine, N-2'-propoxybenzoyl-β-alanine, N-4'-butoxybenzoyl-β-alanine, N-3'-butoxybenzoyl-β-alanine, N-2'-butoxybenzoyl-β-alanine, N-2',4'-dimethoxybenzoyl-β-alanine, N-3',4'-dimethoxybenzoyl-β-alanine, N-3',4',5'-trimethoxybenzoyl-β-alanine, N-2'-hydroxybenzoyl-β-alanine (N-salicyl-β-alanine), N-3'-hydroxybenzoyl-β-alanine, N-4'-hydroxybenzoyl-β-alanine, N-2',4'-dihydroxybenzoyl-β-alanine, N-3',4'-dihydroxybenzoyl-β-alanine, N-3',4',5'-trihydroxybenzoyl-β-alanine (N-galloyl-β-alanine), N-(2'-hydroxy-4'-methoxybenzoyl)-βalanine, N-(3'-hydroxy-4'-methoxybenzoyl)-β-alanine, N-(4'-hydroxy-3'-methoxybenzoyl)-β-alanine, N-2'-methylbenzoyl-βalanine (N-o-toluoyl-β-alanine), N-3'-methylbenzoyl-β-alanine (N-m-toluoyl-β-alanine), N-4'-methylbenzoyl-β-alanine (N-p-toluoyl-β-alanine), N-2'-ethylbenzoyl-β-alanine, N-3'-ethylbenzoyl-β-alanine, N-4'-ethylbenzoyl-β-alanine, N-2'-propylbenzoyl-(β-alanine, N-3'-propylbenzoyl-β-alanine, N-4'-propylbenzoyl-β-alanine, N-phenylacetyl-β-alanine, 4-methoxyphenylacetyl-β-alanine, 3-methoxyphenylacetyl-β-alanine, 2-methoxyphenylacetyl-β-alanine, 4-ethoxyphenylacetyl-β-alanine, 3-ethoxyphenylacetyl-β-alanine, 2-ethoxyphenylacetyl-β-alanine, 2-hydroxyphenylacetyl-β-alanine, 3-hydroxyphenylacetyl-β-alanine, 4-hydroxyphenylacetyl-β-alanine, phenylpropionyl-β-alanine, 4-methoxyphenylpropionyl-β-alanine, 3-methoxyphenylpropionyl-β-alanine, and 2-methoxyphenylpropionyl-β-alanine, as well as these derivatives in which the amino group of the β-alanine segment is N-methylated, N-ethylated, N-propylated, and N-allylated. Although these compounds are preferred because the effect of the present invention will be good, the present invention is not limited to these examples.

It is most preferred that the β-alanine derivative represented by general formula (3) according to the present invention be a β-alanine derivative in which, when one of $R_5$ and $R_6$ is a group represented by the general formula (5), each of $R_7$ through $R_{11}$ is a hydrogen atom, or one or more of $R_7$ through $R_{11}$ is an alkyloxy group with 1-4 carbons, and the (other) ones are hydrogen atoms. Examples may include, for example, N-benzoyl-β-alanine, N-p-anisoyl-β-alanine (N-4'-methoxybenzoyl-β-alanine), N-m-anisoyl-β-alanine (N-3'-methoxybenzoyl-β-alanine), N-o-anisoyl-β-alanine (N-2'-methoxybenzyl-β-alanine), N-p-toluoyl-β-alanine, N-m-toluoyl-β-alanine, N-o-toluoyl-β-alanine, N-3',4',5'-trimethoxybenzoyl-β-alanine, and N-phenylacetyl-β-alanine.

The β-alanine derivative represented by the general formulas (1) through (3) of the present invention may be a salt or a combination forming a salt. Examples of the combination forming a salt may include salts with, for example, alkali metal and alkaline earth metal ions such as sodium, potassium, calcium, zinc, and magnesium; ammonium ions; amine ions such as methylamine, pyridine, trimethylamine, and triethanol amine; acids such as hydrochloric acid, sulfuric acid, phosphoric acid, hydrobromic acid, and alkylsulfuric acids such as methyl sulfuric acid and p-toluenesulfonic acid, as well as acetic acid, lactic acid, maleic acid, fumaric acid, oxalic acid, succinic acid, tartaric acid, and citric acid; and amino acids such as betaine, glycine, serine, and taurine.

A compound selected from the group consisting of N-monomethyl-β-alanine, 3-(1'-piperidine)-propionic acid, β-alanine amide, N-cyclohexyl-β-alanine, N-cyclohexylmethyl-β-alanine, N-cyclohexyl-N-methyl-β-alanine, N-cyclohexylcarbonyl-β-alanine(N-hexahydrobenzoyl-β-alanine), N-(2'-pyridyl)-β-alanine, N-nicotinoyl-β-alanine, N-benzyloxycarbonyl-β-alanine, N-benzyl-β-alanine, N-benzenesulfonyl-β-alanine, N-benzoyl-β-alanine, N-β-anisoyl-β-alanine (N-4'-methoxybenzoyl-β-alanine), N-m-anisoyl-β-alanine (N-3'-methoxybenzoyl-β-alanine), N-o-anisoyl-β-alanine (N-2'-methoxybenzoyl-β-alanine), N-3',4', 5'-trimethoxybenzoyl-β-alanine, and N-phenylacetyl-β-alanine, and salts thereof is the most preferred compound for the β-alanine derivative of the present invention in terms of attaining the object of the present invention wherein the effect of inhibiting parakeratosis, pore shrinkage, and preventing/ameliorating rough skin will be the best, the solubility in the preparation will be good, and the product will be high in safety without any problems such as sensory irritation.

It is a novel feature that the β-alanine derivatives represented by the general formulas (1), (2), or (3) according to the present invention and salts thereof have a parakeratosis-inhibiting function, pore-shrinking function, and rough skin preventing/ameliorating function.

Any of the β-alanine derivatives represented by general formula (1) according to the present invention can be obtained by an easy method such as by introducing the N-substitution group corresponding to β-alanine or an analog corresponding thereto. When the β-alanine derivative represented by general formula (1) according to the present invention is, in particular, 3-(1'-piperidine)-propionic acid, the compound is a publicly known material that can be easily synthesized by publicly known methods and a commercial product thereof can be easily obtained from Aldrich Co.

Any of the β-alanine derivatives represented by general formula (2) according to the present invention can be synthesized by an easy method such as by introducing the amide group corresponding to β-alanine or an analog corresponding thereto. When the β-alanine derivative represented by general formula (2) according to the present invention is, in particular, β-alanine amide hydrochloride salt, the compound is a publicly known material that can be easily synthesized by publicly known methods and a commercial product thereof can be easily obtained from Tokyo Chemical Industry Co., Ltd.

Any of the β-alanine derivatives represented by general formula (3) comprising an alkyl group with 1-7 carbons, alkenyl group with 1-7 carbons, or hydrocarbon group with 3-7 carbons having a cyclic segment can be easily obtained by an easy method such as by introducing the N-alkyl group, N-alkenyl group, or hydrocarbon group having an N-cyclic segment to β-alanine or an analog corresponding thereto.

Although it is possible to synthesize by an easy method a f-alanine derivative represented by general formula (3) and having pyridyl groups, when the β-alanine derivative is, in particular, N-(2'-pyridyl)-β-alanine, the compound is a publicly known material and it particular can be easily synthesized by publicly known methods and a commercial product thereof can be easily obtained from Wako Pure Chemical Industries, Ltd.

Moreover, the β-alanine derivative represented by general formula (3) and having groups represented by general formula (4) can be obtained by easy methods such as introduction of the corresponding N-phenyl group, N-benzyl group, N-phenylethyl group, N-benzenesulfonyl group, N-benzylsulfonyl group, or N-phenylethylsulfonyl group to β-alanine or an analog corresponding thereto; removal of protector groups after introduction of the protected corresponding phenyl group, benzyl group, phenylethyl group, N-benzenesulfonyl group, N-benzylsulfonyl group, or N-phenylethylsulfonyl group; selective alkylation of phenolic hydroxyl groups after introduction of the corresponding phenyl group, benzyl group, phenylethyl group, N-benzenesulfonyl group, N-benzylsulfonyl group, or N-phenylethylsulfonyl group; or introduction of alkyl groups to the aromatic ring by Friedel-Crafts reaction after introduction of the corresponding phenyl, benzyl, phenylethyl, N-benzenesulfonyl, N-benzylsulfonyl, or N-phenylethylsulfonyl group.

Moreover, any of the β-alanine derivatives represented by general formula (3) and having groups represented by general formula (5) can be obtained by easy methods such as introduction of the corresponding N-benzoyl group, N-phenylacetyl group, or N-phenylpropyloyl group to β-alanine or an analog corresponding thereto; removal of protector groups after introduction of the protected corresponding benzoyl group, phenylacetyl group, or phenylpropyloyl group; selective alkylation of phenolic hydroxyl groups after introduction of the corresponding benzoyl group, phenylacetyl group, or phenylpropyloyl group; or introduction of alkyl groups or alkenyl groups to the aromatic ring by Friedel-Crafts reaction after introduction of the corresponding benzoyl group, phenylacetyl group, or phenylpropyloyl group.

In particular, when the β-alanine derivative shown in the general formula (3) that has the groups shown in general formula (5) according to the present invention is N-benzoyl-β-alanine, the compound is a conventional material that can be easily synthesized by conventional methods or can be easily obtained as a commercial product from Tokyo Chemical Industry Co., Ltd.

The following are typical examples of synthesizing the β-alanine derivative according to the present invention, but the present invention is not limited to these examples.

SYNTHESIS EXAMPLES

1) N-o-anisoyl-β-alanine (N-2'-methoxybenzoyl-β-alanine)

Ten grams of β-alanine and 9 g of sodium hydroxide were dissolved in 100 mL of purified water, and 17.4 g of o-anisoylchloride were added dropwise under freezing conditions. After stirring for six hours, hydrochloric acid was added and the pH was adjusted to 2 or less. After extraction with 500 mL of ethyl acetate, the product was desiccated over magnesium sulfate, filtered, and concentrated under reduced pressure. The resulting residue was recrystallized with aqueous ethanol, and 17.0 g of the desired product was obtained (yield of 75%).

2) N-m-anisoyl-β-alanine (N-3'-methoxybenzoyl-β-alanine)

Ten grams of β-alanine and 9 g of sodium hydroxide were dissolved in 100 mL of purified water, and 17.4 g of m-anisoylchloride were added dropwise under freezing conditions. After stirring for five hours, hydrochloric acid was added and the pH was adjusted to 2 or less. After extraction with 500 mL of ethyl acetate, the product was desiccated over magnesium sulfate, filtered, and concentrated under reduced pressure. The resulting residue was recrystallized with aqueous ethanol, and 18.5 g of the desired product was obtained (yield of 81%).

3) N-o-anisoyl-β-alanine (N-4'-methoxybenzoyl-β-alanine)

Ten grams of β-alanine and 9 g of sodium hydroxide were dissolved in 100 mL of purified water, and 17.4 g of p-anisoylchloride were added dropwise under freezing conditions. After stirring for five hours, hydrochloric acid was added and the pH was adjusted to 2 or less. After extraction with 500 mL of ethyl acetate, the product was desiccated over magnesium sulfate, filtered, and concentrated under reduced pressure. The resulting residue was recrystallized with aqueous ethanol, and 19.1 g of the desired product was obtained (yield of 84%).

4) N-cyclohexylcarbonyl-β-alanine (N-hexahydrobenzoyl-β-alanine)

Ten grams of β-alanine and 9 g of sodium hydroxide were dissolved in 100 mL of purified water, and 14.9 g of cyclohexanecarbonyl chloride were added dropwise under freezing conditions. After stirring for five hours, hydrochloric acid was added and the pH was adjusted to 2 or less. After extraction with 500 mL of ethyl acetate, the product was desiccated over magnesium sulfate, filtered, and concentrated under reduced pressure. The resulting residue was recrystallized with aqueous ethanol, and 17.2 g of the desired product was obtained (yield of 85%).

5) N-nicotinoyl-β-alanine

Ten grams of β-alanine and 9 g of sodium hydroxide were dissolved in 100 mL of purified water, and 18.15 g of nicotinoyl chloride hydrochloride were added dropwise under freezing conditions. After stirring for five hours, the product was filtered, the resulting crude product was recrystallized with aqueous ethanol, and 19.1 g of the desired product was obtained (yield of 84%).

6) N-benzyl-β-alanine

Ten grams of β-alanine ethyl ester hydrochloride and 9 g of benzaldehyde were added to 100 mL of toluene and heated and refluxed using a Dean-Stark trap. After heating and stirring for three hours, the product was cooled in air, and the reaction system was concentrated under reduced pressure. 200 mL of ethanol were added to the resulting residue, and 5 g of sodium borohydride were added while stirring under freezing conditions. After stirring over a period of one night, hydrochloric acid was added and the pH was brought to 2 or less. After filtering, the product was concentrated under reduced pressure, the resulting residue was dissolved in 200 mL THF-water, and 2 g of sodium hydroxide were added. After stirring for six hours at room temperature, the product was neutralized with Amberlite IR120B[H] and filtered, and the filtrate was concentrated under reduced pressure. The resulting residue was recrystallized to obtain 8.2 g f the desired product (yield of 70%).

7) N-methyl-β-alanine

After methylamine was blown into 10 mL of pyridine, 1 g of β-bromopropionic acid was added, and the reactants were reacted overnight in a sealed vessel at 90° C. The reaction system was concentrated under reduced pressure. 20 mL of ethanol were added to the resulting residue, the product was neutralized with Amberlite IR120B[H] and then filtered, and the filtrate was concentrated under reduced pressure. The resulting residue was recrystallized to obtain 890 mg of the desired product (yield of 80%).

8) N-cyclohexyl-β-alanine 22 g of cyclohexylamine were added to 40 mL of ethanol, 10 g of ethyl 3-bromopropionate were added, and the mixture was heated and refluxed for two hours. The reaction system was concentrated under reduced pressure, the resulting residue was extracted with 200 mL of ethyl acetate, the organic layer was desiccated over anhydrous magnesium sulfate, and the product was then filtered and concentrated. The residue was purified by distillation under reduced pressure, and 6.3 g of N-cyclohexylmethyl β-alanine ethyl ester (yield of 57%) were obtained. 1.26 g of sodium hydroxide were dissolved in 200 mL of water, 6.3 g of N-cyclohexyl-β-alanine ethyl ester were added, and THF was added for dissolution. After stirring for one hour, the product was neutralized using Dowex 50WX4-[H$^+$] and filtered, and the filtrate was concentrated under reduced pressure. The resulting residue was recrystallized and 3.2 g of the desired product were obtained (yield of 64%).

9) N-cyclohexyl-β-alanine 22 g of cyclohexylmethylamine were added to 40 mL of ethanol, 10 g of ethyl p-bromopropionate were added, and the mixture was heated and refluxed for two hours. The reaction system was concentrated under reduced pressure, the resulting residue was extracted with 200 mL of ethyl acetate, the organic layer was desiccated over anhydrous magnesium sulfate, and the product was then filtered and concentrated. The residue was purified by distillation under reduced pressure, and 9.7 g of N-cyclohexylmethyl-β-alanine ethyl ester (yield of 82%) were obtained. 1.81 g of sodium hydroxide were dissolved in 200 mL of water, 9.7 g of N-cyclohexylmethyl-β-alanine ethyl ester were added, and THF was added for dissolution. After stirring for one hour, the product was neutralized using Dowex 50WX4-[H$^+$] and filtered, and the filtrate was concentrated under reduced pressure. The resulting residue was recrystallized and 6.7 g of the desired product were obtained (yield of 80%).

10) N-cyclohexyl-N-methyl-β-alanine 22 g of N-methylcyclohexylamine were added to 40 mL of ethanol, 10 g of ethyl β-bromopropionate were added, and the mixture was heated and refluxed for two hours. The reaction system was concentrated under reduced pressure, the resulting residue was extracted with 200 mL of ethyl acetate, the organic layer was desiccated over anhydrous magnesium sulfate, and the product was then filtered and concentrated. The residue was purified by distillation under reduced pressure, and 9.4 g of N-cyclohexyl-N-methyl β-alanine ethyl ester (yield of 80%) were obtained. 1.75 g of sodium hydroxide were dissolved in 200 mL of water, 9.4 g of N-cyclohexylmethyl-N-methyl-β-alanine ethyl ester were obtained, and THF was added for dissolution. After stirring for one hour, the product was neutralized using Dowex 50WX4-[H$^+$] and filtered, and the filtrate was concentrated under reduced pressure. The resulting residue was recrystallized and 6.7 g of the desired product were obtained (yield of 82%).

11) N-benzenesulfonyl-β-alanine

Ten grams of β-alanine and 9 g of sodium hydroxide were dissolved in 100 mL of purified water, 17.4 g of sulfonyl chloride were added dropwise under freezing conditions, and then the product was stirred for six hours. After washing with 200 mL of ethyl acetate; hydrochloric acid was added to bring the mixture to approximate neutrality; the mixture was extracted using 500 mL of ethyl acetate; the product was desiccated over magnesium sulfate, filtered, and then concentrated under reduced pressure; the resulting residue was recrystallized using aqueous ethanol; and 17.0 g of the desired product was obtained (yield of 75%).

A β-alanine derivative or a salt thereof as represented by the general formula (1), (2), or (3) according to the present invention has an excellent parakeratosis-inhibiting function, pore-shrinking function, and rough skin preventing/ameliorating function, as will be later shown. Consequently, one, two, or more compounds selected from the group consisting of β-alanine derivatives represented by the general formula (1), (2), or (3) according to the present invention and salts thereof (one, two, or more of compounds selected from the group consisting of β-alanine derivatives represented by the general formula (1), (2), or (3) according to the present invention and salts thereof are also referred to as "β-alanine derivatives" hereafter) are useful as a parakeratosis inhibitor, pore-shrinking agent, and rough skin preventing/ameliorating agent.

Such a β-alanine derivatives is contained as an active ingredient and is useful as a parakeratosis inhibitor, pore-shrinking agent, or rough skin preventing/ameliorating agent. This parakeratosis inhibitor, pore-shrinking agent, and rough skin preventing/ameliorating agent is preferably used externally on skin, and, for instance, improves conspicuous pores on the nose and cheeks and prevents or abates rough skin when used on the face, improves conspicuous pores and prevents or abates rough skin after hair removal treatment of the legs and the like when used on the body.

The parakeratosis inhibitor, pore-shrinking agent, and rough skin preventing/ameliorating agent is a novel and useful application based on the discovery of the above-mentioned novel function of the β-alanine derivatives according to the present invention.

The parakeratosis inhibitor, pore-shrinking agent, and rough skin preventing/ameliorating agent of the present invention are high in safety; therefore, they have a very wide application range and can be used in a variety of fields. Such fields may be found, for example, in fields that include cosmetics containing pharmaceutical external products, pharmaceutical products, and food products.

Moreover, β-alanine derivatives that are the parakeratosis inhibitor, pore-shrinking agent, or rough skin preventing/ameliorating agent of the present invention are not sensory irritants and are each added to an external composition for skin to thereby prepare an external composition for skin having a function such as parakeratosis inhibition, pore shrinkage, or rough skin prevention/abatement.

This external composition for skin containing a β-alanine derivative as a parakeratosis inhibitor, pore-shrinking agent, or rough skin preventing/ameliorating agent according to the present invention is novel and high in safety, and it can be used as an external composition for skin that has a parakeratosis-inhibiting effect, pore-shrinking effect, and rough skin-preventing/ameliorating effect.

The external composition for skin according to the present invention can be used in pore-shrinking agents; facial cosmetics for improving conspicuous pores on the nose, cheeks, and the like; facial cosmetics for preventing or ameliorating rough skin; and skin external preparations for the body for improving conspicuous pores after hair removal treatment of legs and the like.

When the β-alanine derivatives of the present invention are included in the composition of a parakeratosis inhibitor, pore-shrinking agent, rough skin preventing/ameliorating agent, or external composition for skin and the like, the β-alanine derivatives of the present invention are included in an amount that is effective for showing the relevant function. This content is preferably 0.001 to 20.0 mass %, more preferably 0.01 to 10.0 mass %, and particularly preferably 0.2 to 5.0 mass %, in relation to the total amount of the composition. When a mixture of the β-alanine derivatives of the present invention and salts thereof is used, the maximum total content is preferably 20.0 mass % or less, more preferably 10.0 mass % or less, and particularly preferably 5.0 mass % or less.

To the composition of parakeratosis inhibitor, pore-shrinking agent, rough skin preventing/ameliorating agent, external preparation for skin and the like, according to the present invention, there may be optionally added as needed components normally used for external preparations for skin such as common cosmetics, Preparation Examples and the like such as, for examples, oils, surfactants, powders, pigments, water, alcohols, thickeners, chelating agents, silicones, oxidation inhibitors (antioxidants), UV absorbers, humectants, perfumes, various pharmaceutical components, preservatives, neutralizers, and pH regulators.

Of these optional components, examples of oils are liquid oils and fats such as avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, moonflower oil, perilla oil, soy oil, peanut oil, tea seed oil, Japanese nutmeg oil, rice germ oil, tung oil, Japanese foxglove oil, jojoba oil, germ oil, triglycerin, glycerin trioctanoate, and glycerin triisopalmitate; solid oils and fats such as cocoa fat, coconut oil, equine tallow, hydrogenated coconut oil, palm oil, bovine tallow, ovine tallow, hydrogenated bovine tallow, palm seed oil, porcine tallow, vegetable wax seed oil, hydrogenated oil, vegetable wax, and hydrogenated castor oil; waxes such as beeswax, candelilla wax, carnauba wax, lanolin, lanolin acetate, liquid lanolin, cane wax, isopropyl lanolin fatty acid, hexyl laurate, reduced lanolin, jojoba wax, hydrogenated lanolin, polyoxyethylene (hereinafter, POE) lanolin alcohol ether, POE lanolin alcohol acetate, lanolin fatty acid polyethylene glycol, and POE hydrogenated lanolin alcohol ether; hydrocarbons such as liquid paraffin, ozokerite, squalene, paraffin, seresin, squalane, Vaseline, and microcrystalline wax;

ester oils such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid esters, N-alkylglycol monoisostearate, neopentyl glycol dicaprate, diisostearyl malate, glycerin di-2-heptyl undecanoate, trimethylolpropane tri-2-ethylhexylate, trimethylolpropane triisostearate, pentaerythritol tetra-2-ethylhexylate, glycerin tri-2-ethylhexylate, trimethylolpropane triisostearate, cetyl-2-ethylhexanoate, 2-ethylhexyl palmitate, glycerin trimyristate, glyceride tri-2-heptylundecanoate, castor oil fatty acid methyl ester, oleic acid oil, acetoglyceride, 2-heptylundecyl palmitate, diisopropyl adipate, N-lauroyl-L-glutamic acid-2-octyldodecyl ester, di-2-heptylundecyl adipate, di-2-ethylhexyl sebacate, 2-hexyldecyl myristate, 2-hexyldecyl palmitate, 2-hexyldecyl adipate, diisopropyl sebacate, and 2-ethylhexyl succinate; higher fatty acids such as lauric acid, myristic acid, palmitic acid, stearic acid, behenic acid, oleic acid, 12-hydroxystearic acid, undecylenic acid, lanolin fatty acid, isostearic acid, linolic acid, linoleic acid, and eicosapentaenoic acid; straight or branched higher alcohols such as lauryl alcohol, cetyl alcohol, stearyl alcohol, behenyl alcohol, myristyl alcohol, oleyl alcohol, cetostearyl alcohol, monostearyl glycerin ether (batyl alcohol), 2-decyl tetradecinol, lanolin alcohol, cholesterol, phytosterol, hexyl dodecanol, isostearyl alcohol, and octyl dodecanol; silicone oils such as dimethyl polysiloxane and methylphenyl polysiloxane; and perfluorocarbons or perfluoropolyethers such as perfluorohexane and triperfluoro-n-butylamine.

Examples of surfactants include: as anionic surfactants, fatty acid soaps such as raw soap, sodium laurate, and palmitic acid; higher alkyl sulfuric acid ester salts such as sodium laurylsulfate and potassium laurylsulfate; alkyl ether sulfuric acid ester salts such as POE triethanolamine lauryl sulfate and POE sodium lauryl sulfate; N-acylsarcosinic acids such as sodium lauroylsarcosinate; higher fatty acid amide sulfonates such as N-myristoyl-N-methyltaurine sodium and coconut oil fatty acid methyl taurate sodium; phosphoric acid ester salts such as POE stearyl ether phosphate; sulfosuccinates such as sodium monolauroyl monomethanol amide POE sulfosuccinate and sodium lauryl polypropylene glycol sulfosuccinate; alkylbenzenesulfonates such as sodium linear dodecylbenzenesulfonate and triethanolamine linear dodecylbenzenesulfonate;

N-acylglutamates such as disodium N-stearoylglutamate and monosodium N-stearoylglutamate; higher fatty acid ester sulfuric acid ester salts such as hydrogenated coconut oil fatty acid glycerin sodium sulfate; and sulfated oils such as Turkey red oil; and anionic surfactants such as POE alkyl ether carboxylic acid, POE alkyl allyl ether carboxylic acid, higher fatty acid ester sulfonate, secondary alcohol sulfuric acid ester salt, higher fatty acid alkylol amide sulfuric acid ester salt, lauroylmonoethanolamide sodium succinate, and casein sodium; as cationic surfactants, alkyl trimethylammonium salts such as stearyltrimethyl ammonium chloride and lauryltrimethylammonium chloride; dialkyldimethylammonium salts such as distearyldimethylammonium chloride salt; and alkylpyridinium salts such as cetylpyridinium chloride; cationic surfactants such as alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, and benzalkonium chloride;

as amphoteric surfactants, imidazoline amphoteric surfactants such as 2-cocoyl-2-imidazolinium hydroxide-1-carboxyethyloxy disodium salt, and betaine surfactants such as amidobetaine and sulfobetaine;

as hydrophobic nonionic surfactants, sorbitan fatty acid esters such as sorbitan monooleate, sorbitan monoisostearate, sorbitan monolaurate, sorbitan monopalmitate, and sorbitan trioleate; glycerin polyglycerin fatty acids such as mono-cottonseed oil fatty acid glycerin, glycerin monostearate, glycerin sesquioleate, and glycerin malate monostearate; propylene glycol fatty acid esters such as propylene glycol monostearate; and hydrophobic nonionic surfactants such as hydrogenated castor oil derivatives, glycerin alkyl ether, and POE-methylpolysiloxane copolymers;

as hydrophilic nonionic surfactants, POE sorbitan fatty acid esters such as POE sorbitan monooleate and POE sorbitan monostearate; POE sorbitol fatty acid esters such as POE sorbitol monolaurate, POE sorbitol monooleate, and POE sorbitol monostearate; POE glycerin fatty acid esters such as POE glycerin monooleate and POE glycerin distearate; POE fatty acid esters such as POE monooleate, POE distearate, and POE monodioleate; POE alkyl ethers such as POE lauryl ether, POE oleyl ether, and POE cholestanol ester; POE alkylphenyl ethers such as POE octylphenyl ether and POE nonylphenyl ether;

POE-polyoxypropylene (hereinafter POP hereinafter) alkyl ethers such as POE polyoxypropylene monobutyl ether, POE-POP cetyl ether, and POE-POP glycerin ether; POE castor oil hydrogenated castor oil derivatives such as POE castor oil, POE hydrogenated castor oil, POE hydrogenated castor oil monoisostearate, and POE hydrogenated castor oil maleate; POE beeswax lanolin derivatives such as POE sorbitol beeswax; alkanolamides such as coconut oil fatty acid diethanolamide and fatty acid isoproponolamide; as well as hydrophilic nonionic surfactants such as POE propylene glycol fatty acid ester, POE fatty acid amide, POE alkylamine, sucrose fatty acid ester, and alkyl ethoxydimethylamine oxide.

Examples of powders may include, for example, mica, talc, kaolin, sericite (fine grained mica), muscovite, phlogopite, synthetic mica, lepidolite, biotite, lithia mica, synthetic mica, calcium carbonate, magnesium carbonate, silicic anhydride (silica), aluminum silicate, barium silicate, calcium silicate, magnesium silicate, strontium silicate, aluminum oxide, barium sulfate, Indian red, yellow iron oxide, black iron oxide, cobalt oxide, ultramarine, Prussian blue, titanium oxide, zinc oxide, mica titanium (titanium oxide-coated mica), aluminum foil, bismuth oxychloride, boron nitride, red No. 228, red No. 226, blue No. 404, polyethylene powder, polymethyl methacrylate powder, polyamide resin powder (nylon powder), cellulose powder, organopolysiloxane elastomer, aluminum powder, and copper powder.

Examples of alcohols may include, for example, lower alcohols such as methanol, ethanol, propanol, isopropanol; cholesterol, sitosterol, and lanosterol.

Examples of thickeners may include, for example, eater-soluble polymers such as: vegetable polymers such as gum arabic, tragacanth gum, galactan, carob gum, guar gum, carrageenan, pectin, agar, and starch (corn, wheat, potato, rice); microbiological polymers such as dextran and pullulan; starch polymers such as carboxymethyl starch and methyl hydroxypropyl starch; animal polymers such as collagen, casein, and gelatin; cellulose polymers such as methyl cellulose, nitrocellulose, ethyl cellulose, hydroxyethyl cellulose, sodium sulfate cellulose, hydroxypropyl cellulose, carboxymethyl cellulose, and crystalline cellulose; alginic acid polymers such as sodium alginate and propylene glycol alginate ester; vinyl polymers such as polyvinyl methyl ether and carboxyvinyl polymer; acrylic polymers such as POE polymers, POE polyoxypropylene copolymer polymers, sodium polyacrylate, polyacrylamide; and inorganic water-soluble polymer such as polyethylene imine, cationic polymers, bentonite, aluminum magnesium silicate, laponite, hectorite, and anhydrous silicic acid.

Examples of chelating agents may include, for example, citramalic acid, agaric acid, glyceric acid, shikimic acid, hinokitiol, gallic acid, tannic acid, caffeic acid, ethylenediamine tetraacetic acid, ethylene glycol diamine tetraacetic acid, diethylene triamine pentaacetic acid, phytic acid, polyphosphoric acid, and metaphosphoric acid, as well as analogs and alkali metal salts and carboxylic acid esters thereof.

Examples of UV absorbers may include, for example, benzoic acid UV absorbers such as paraminobenzoic acid; anthranilic acid UV absorbers such as methyl anthranyl; salicylic acid UV absorbers such as octyl salicylate; cinnamic acid UV absorbers such as isopropyl paramethoxycinnamic acid and octyl paramethoxycinnamic acid; and UV absorbers such as urocanic acid and ethyl urocanate.

Examples of humectants may include, for example, polyethylene glycol (hereinafter, PEG), propylene glycol, dipropylene glycol, 1,3-butylene glycol, glycerin, diglycerin, xylitol, maltitol, maltose, D-mannitol, glucose, fructose, sodium chondroitin sulfate, sodium hyaluronic acid, sodium lactate, glucosamine, and cyclodextrin.

Examples of pharmaceutical components that can be added may include, for example, vitamins such as vitamin A oil, retinol, retinol palmitate, pyridoxine hydrochloride, benzyl nicotinate, nicotinamide, dl-α-tocopherol nicotinate, magnesium ascorbic phosphate, vitamin $D_2$, dl-α-tocopherol, pantothenic acid, and biotin; anti-inflammatory agents such as azulene and glycyrrhizic acid; skin whiteners such as arbutin; hormones such as estradiol; astringents such as zinc oxide and tannic acid; refrigerants such as L-menthol and camphor; lysozyme hydrochloride; pyridoxine hydrochloride; and sulfur. It is also possible to add a variety of extracts that show diverse pharmaceutical efficacies. Examples may include, for example, dokudami extract, phellodendron extract, glycyrrhiza extract, peony root extract, moutan bark extract, luffa extract, saxifrage extract, eucalyptus extract, clove flower extract, horse chestnut extract, cornflower extract, algae extract, and thyme extract.

Examples of preservatives may include, for example, benzoic acid, salicylic acid, paraoxybenzoic acid esters (methyl paraben, ethyl paraben, and butyl paraben), sorbic acid, parachlorometacresol, hexachlorophene, benzalkonium chloride, chlorhexidine chloride, trichlorocarbanilide, photosensitizers, and phenoxyethanol.

Examples of other additives that can be added to Preparation Examples of the present invention may include, for example, neutralizers such as 2-amino-2-methyl-1-propanol, 2-amino-2-methyl-1,3-propanediol, potassium hydroxide, potassium hydroxide, triethanolamine, and sodium carbonate; pH regulators such as lactic acid, citric acid, glycolic acid, succinic acid, tartaric acid, malic acid, sodium bicarbonate, and ammonium bicarbonate; and antioxidants such as ascorbic acid, α-tocopherol, and carotenoids.

The above-mentioned components are examples, and the present invention is not limited to these examples. These components can be added in any combination in accordance with a preparation that conforms to a predetermined form.

The composition of the present invention, such as a parakeratosis inhibitor, pore-shrinking agent, rough skin preventing/ameliorating agent, and external composition for skin, can be widely used in the form of a pharmaceutical product, a pharmaceutical external product (ointment, dentifrice, and the like), or a cosmetic (fundamental cosmetic such as a face wash, milky lotion, cream, gel, essence (clarifier), pack, and mask; basic skin care products; makeup such as foundation or lipstick; oral cosmetic; perfume cosmetic; hair cosmetic product; body cosmetic; and the like). The form of composition of the present invention, such as a parakeratosis inhibitor, pore-shrinking agent, rough skin preventing/ameliorating agent, or external composition for skin, is not limited to these forms.

The dosage form can be obtained in a variety of dosage forms, including aqueous solutions, solubilized forms, emulsions, oils, gels, ointments, aerosols, water-oil two-layer forms, water-oil-powder three-layer forms, and the like.

By using the composition of the present invention, such as the parakeratosis inhibitor, pore-shrinking agent, rough skin preventing/ameliorating agent, or external composition for skin, it is possible to prevent parakeratosis and maintain or improve skin to a healthy state, and to further shrink pores, thereby providing a skin with a youthful and fresh appearance with less conspicuous pores.

EXAMPLES

The present invention will now be described using the following examples. Unless otherwise stated, the amounts added are by mass %.

Example 1

Parakeratosis-Inhibiting Effect Tests

Aqueous solutions (containing 30 mass % of ethanol) of 3 mass % of a β-alanine derivative or salt thereof were prepared mainly as the evaluation sample. The pH was regulated by hydrochloric acid or sodium hydroxide so as to be 7.0 to 7.5. When sample solubility was low, the solution was prepared accordingly.

100 μL of 10 mass % oleic acid solution (solvent: ethanol) were applied to the back of a hairless mouse (HR-1; Hoshino Laboratory Animals). Then the sample solution (β-alanine derivative, and the like) was applied 100 μL at a time. This procedure was continued for three days. On the following day, the status of the back skin was observed with a CCD camera, and the rough skin status (peeling and redness of the stratum corneum) was visually evaluated. The status of the skin was evaluated in 0.25-point intervals: with the skin where the control (control aqueous solution) had been applied being 2.0; and the skin where there was no skin roughness being 0.0. At the same time, the stratum corneum at the back of the hairless mouse was peeled off with tape, the nuclei were stained by hematoxylin, and the degree of parakeratosis was observed and evaluated by a parakeratosis value within a range of 1.0 to 3.0 (in 0.25 increments). An increase in the value indicates that there are many nucleated cells in the stratum corneum, i.e., that parakeratosis is advanced. The results are shown in Table 1.

TABLE 1

| Sample | Concentration (mass %) | Visual evaluation (average of four animals) | Parakeratosis value (average of four animals) |
|---|---|---|---|
| Aqueous control solution | — | 2.0 | 2.0 |
| N-methyl-β-alanine | 3 | 1.1 | 1.2 |
| N-benzoyl-β-alanine | 3 | 1.1 | 1.1 |
| N-(4'-methoxybenzoyl-β-alanine | 1.5 | 1.2 | 1.1 |
| N-(3'-methoxybenzoyl-β-alanine | 3 | 1.2 | 1.2 |
| N-(2'-methoxybenzoyl-β-alanine | 3 | 1.1 | 1.1 |
| 3-(1'-piperidine)-propionate | 3 | 1.4 | 1.4 |
| N-(3',4',5'-trimethoxybenzoyl)-β-alanine | 3 | 1.1 | 1.1 |
| N-benzyl-β-alanine | 3 | 1.2 | 1.2 |
| N-benzenesulfonyl-β-alanine | 3 | 1.1 | 1.2 |
| N-cyclohexyl-β-alanine | 3 | 1.1 | 1.1 |
| N-cyclohexylmethyl-β-alanine | 3 | 1.1 | 1.1 |
| N-cyclohexyl-N-methyl-β-alanine | 3 | 1.4 | 1.4 |
| N-cyclohexylcarbonyl-β-alanine | 3 | 1.1 | 1.2 |
| N-(2'-pyridyl)-β-alanine | 3 | 1.4 | 1.3 |
| N-nicotinoyl-β-alanine | 1 | 1.1 | 1.2 |
| β-alanine amide hydrochloride salt | 3 | 1.3 | 1.3 |

TABLE 1-continued

| Sample | Concentration (mass %) | Visual evaluation (average of four animals) | Parakeratosis value (average of four animals) |
|---|---|---|---|
| N-acetyl-β-alanine (Comparative Example) | 3 | 1.8 | 1.7 |
| 3-ureidopropionic acid (Comparative Example) | 3 | 2.0 | 2.2 |
| 3-guanidinopropionic acid (Comparative Example) | 3 | 2.1 | 2.1 |

As is clear from Table 1, a rough skin preventing effect, based on stratum corneum peeling and redness, was seen in case of N-methyl-β-alanine, N-benzoyl-β-alanine, N-(4'-methoxybenzoyl)-β-alanine, N-(3'-methoxybenzoyl)-β-alanine, N-(2'-methoxybenzoyl)-β-alanine, 3-(1'-piperidine)-propionate, N-(3',4',5'-methoxybenzoyl)-β-alanine, N-benzyl-β-alanine, N-benzenesulfonyl-β-alanine, N-cyclohexyl-β-alanine, N-cyclohexylmethyl-β-alanine, N-cyclohexyl-N-methyl-β-alanine, N-cyclohexylcarbonyl-β-alanine, N-(2'-pyridyl)-β-alanine, N-nicotinoyl-β-alanine, and β-alanine amide hydrochloride salt. They also reduced the parakeratosis value. Therefore, the above-mentioned compounds were recognized to have a parakeratosis-inhibiting effect. On the other hand, an effect was not seen in case of the acetylated β-alanine (N-acetyl-β-alanine) which does not have a benzene ring. Similarly, an effect was not seen in case of 3-ureidopropionic acid, even though the amino group of the β-alanine does have a carbonyl group. An effect was not seen in case of 3-guanidinopropionic acid in which the oxygen atoms of the carbonyl groups are substituted by nitrogen atoms.

Example 2

Human Pore-Shrinking Effect

An experiment was conducted whereby a sample was applied twice a day for one month to the cheeks of healthy human males in groups of 5 men each. Aqueous solutions (containing 15 mass % of ethanol) of 3 mass % of the β-alanine derivative or a salt thereof were prepared mainly as the evaluation sample. The pH was regulated by hydrochloric acid or sodium hydroxide so as to be 7.0 to 7.5. When the sample solubility was low, the solution was prepared accordingly. The control was an aqueous 15% ethanol solution. The sample aqueous solution and the control aqueous solution were applied to one half of the face at a time.

A replica was collected before and after continuous application, and changes in the shape of the pores at the same site were observed using a three-dimensional laser scanning microscope. The size of the pores was visually evaluated in the 13 steps of 1 through 13 (with the pores becoming larger as the numbers became larger), the difference in the ratings before and after application (after application—before application) was calculated, and the efficacy of each sample was studied using this difference as the replica assessment value. The results are shown in Table 2.

TABLE 2

| Sample | Concentration (mass %) | Replica assessment value (average of n = 5) |
|---|---|---|
| Control aqueous solution | — | 0.3 |
| N-methyl-β-alanine | 3 | −1.0 |
| N-benzoyl-β-alanine | 1.0 | −1.5 |
| N-(4'-methoxybenzoyl)-β-alanine | 1.0 | −1.2 |
| N-(3'-methoxybenzoyl)-β-alanine | 3 | −1.0 |
| N-(2'-methoxybenzoyl)-β-alanine | 3 | −0.9 |
| 3-(1'-piperidine)-propionate | 3 | −1.2 |
| N-(3',4',5'-trimethoxybenzoyl)-β-alanine | 3 | −0.6 |
| N-benzyl-β-alanine | 3 | −0.8 |
| N-benzenesulfonyl-β-alanine | 3 | −0.7 |
| N-cyclohexyl-β-alanine | 3 | −0.9 |
| N-cyclohexylmethyl-β-alanine | 3 | −0.8 |
| N-cyclohexyl-N-methyl-β-alanine | 3 | −0.8 |
| N-cyclohexylcarbonyl-β-alanine | 3 | −0.6 |
| N-(2'-pyridyl)-β-alanine | 3 | −0.8 |
| N-nicotinoyl-β-alanine | 1 | −0.8 |
| β-alanine amide hydrochloride salt | 3 | −0.3 |

As is clear from Table 2, a pore-shrinking effect was seen in case of N-methyl-β-alanine, N-benzoyl-β-alanine, N-(4'-methoxybenzoyl)-β-alanine, N-(3'-methoxybenzoyl)-β-alanine, N-(2'-methoxybenzoyl-β-alanine, 3-(1'-piperidine)-propionate, N-(3',4',5'-trimethoxybenzoyl)-β-alanine, N-benzyl-β-alanine, N-benzenesulfonyl-β-alanine, N-cyclohexyl-β-alanine, N-cyclohexylmethyl-β-alanine, N-cyclohexyl-N-methyl-β-alanine, N-cyclohexylcarbonyl-β-alanine, N-(2'-pyridyl)-β-alanine, N-nicotinoyl-β-alanine, and β-alanine amide hydrochloride salt.

Example 3

Inhibiting Effect on Rough Skin Induced by Oleic Acid Application

In order to investigate the inhibiting effect of β-alanine derivatives and salts thereof on rough skin induced by oleic acid application, the transepidermal water loss (TEWL value) before and after application was measured, the difference was compared with the control (control aqueous solution), and the effect was determined. Sample preparation and the application method were in accordance with that of Example 1. The TEWL was determined using the TM210 TEWA Meter (Courage+Khazaka Electronic GmBH).

100 μL of 10 mass % oleic acid (solvent: ethanol) was applied to the back of hairless mice (HR-1, four mice per group). Then a sample solution (β-alanine derivatives) was applied 100 μL at a time. This procedure was continued for three days. On the following day, the TEWL value of the back was determined and the values of the four animals were averaged. The results are shown in Table 3. An increase in ΔTEWL value indicates that the rough skin became worse.

TABLE 3

| Sample | Concentration (mass %) | ΔTEWL value |
|---|---|---|
| Control aqueous solution | — | 12.0 |
| N-methyl-β-alanine | 3 | 6.8 |
| N-benzoyl-β-alanine | 3 | 4.0 |
| N-(4'-methoxybenzoyl)-β-alanine | 1.5 | 5.7 |
| N-(3'-methoxybenzoyl)-β-alanine | 3 | 6.9 |
| N-(2'-methoxybenzoyl)-β-alanine | 3 | 7.0 |
| 3-(1'-piperidine)-propionate | 3 | 5.5 |
| N-(3',4',5'-trimethoxybenzoyl)-β-alanine | 3 | 6.9 |

TABLE 3-continued

| Sample | Concentration (mass %) | ΔTEWL value |
|---|---|---|
| N-benzyl-β-alanine | 3 | 8.9 |
| N-benzenesulfonyl-β-alanine | 3 | 5.4 |
| N-cyclohexyl-β-alanine | 3 | 9.0 |
| N-cyclohexylmethyl-β-alanine | 3 | 8.9 |
| N-cyclohexyl-N-methyl-β-alanine | 3 | 5.5 |
| N-cyclohexylcarbonyl-β-alanine | 3 | 8.0 |
| N-(2'-pyridyl)-β-alanine | 3 | 5.5 |
| N-nicotinoyl-β-alanine | 1 | 6.0 |
| β-alanine amide hydrochloride salt | 3 | 8.9 |
| N-acetyl-β-alanine (Comparative Example) | 3 | 12.1 |
| N-ureidopropionic acid (Comparative Example) | 3 | 11.9 |
| N-guanidinopropionic acid (Comparative Example) | 3 | 12.3 |

As is clear from Table 3, the ΔTEWL value was significantly lower than that with the control aqueous solution, and a rough skin preventing/ameliorating effect was seen by application of N-methyl-β-alanine, N-benzoyl-β-alanine, N-(4'-methoxybenzoyl)-β-alanine, N-(3'-methoxybenzoyl)-β-alanine, N-(2'-methoxybenzoyl)-β-alanine, 3-(1'-piperidine)-propionate, N-(3',4',5'-methoxybenzoyl)-β-alanine, N-benzyl-β-alanine, N-benzenesulfonyl-(β-alanine, N-cyclohexyl-β-alanine, N-cyclohexylmethyl-β-alanine, N-cyclohexyl-N-methyl-β-alanine, N-cyclohexylcarbonyl-β-alanine, N-(2'-pyridyl)-β-alanine, N-nicotinoyl-β-alanine, and β-alanine amide hydrochloride salt. On the other hand, no effect was seen in case of the acylated β-alanine (N-acetyl-β-alanine) with no benzenring. Similarly, no effect was seen in case of 3-ureidopropionic acid, even though the amino group of the β-alanine had a carbonyl group. Also, no effect was seen in case of 3-guanidinopropionic acid in which, the oxygen atom of the carbonyl group was substituted by nitrogen atoms.

Example 4

Sensory Irritation Tests 1 mL of a control aqueous solution and the sample aqueous solution prepared in Example 1 were applied using a cotton swab to the left or right cheek, respectively, of each member of a panel of 20 women, and the irritating sensation was evaluated every 30 seconds for ten minutes beginning immediately after application, whereby a final evaluation was reported. The evaluation of the irritating sensation was made based on the following four levels of rating criteria, and the average rating was calculated, whereby the average was classified by the following criteria.

(Rating Criteria)

3: Continuation is not possible because of extremely strong irritation, such as tingling sensation, burning sensation, stinging sensation, itching, and the like.

2: Intolerable because of strong irritation, such as tingling sensation, burning sensation, stinging sensation, itching, and the like.

1: Tolerable, but with slight irritation such as tingling sensation, burning sensation, stinging sensation, itching, and the like.

0: Not particularly irritating.

(Evaluation Criteria)

A: average rating of less than 0.2
B: average rating of from 0.2 to less than 1.0
C: average rating of from 1.0 to less than 2.0
D: average rating of 2.0 or greater The results are shown in Table 4.

TABLE 4

| Sample | Concentration (mass %) | Evaluation |
|---|---|---|
| Control aqueous solution | — | — |
| N-methyl-β-alanine | 3 | A |
| N-benzoyl-β-alanine | 3 | A |
| N-(4'-methoxybenzoyl)-β-alanine | 1.5 | A |
| N-(3'-methoxybenzoyl)-β-alanine | 3 | A |
| N-(2'-methoxybenzoyl)-β-alanine | 3 | A |
| 3-(1'-piperidine)-propionate | 3 | A |
| N-(3',4',5'-trimethoxybenzoyl)-β-alanine | 3 | A |
| N-benzyl-β-alanine | 3 | A |
| N-benzenesulfonyl-β-alanine | 3 | A |
| N-cyclohexylmethyl-β-alanine | 3 | A |
| N-cyclohexyl-N-methyl-β-alanine | 3 | A |
| N-cyclohexylcarbonyl-β-alanine | 3 | A |
| N-(2'-pyridyl)-β-alanine | 3 | A |
| N-nicotinoyl-β-alanine | 1 | A |
| β-alanine amide hydrochloride salt | 3 | A |
| alanine (Comparative Example) | 3 | D |

As is clear from Table 4, it was confirmed that no problem of sensory irritation was seen and the safety is high in case of N-methyl-β-alanine, N-benzoyl-β-alanine, N-(4'-methoxybenzoyl-β-alanine, N-(3'-methoxybenzoyl)-β-alanine, N-(2'-methoxybenzoyl-β-alanine, 3-(1'-piperidine)-propionate, N-(3',4',5'-methoxybenzoyl)-β-alanine, N-benzyl-β-alanine, N-benzenesulfonyl-β-alanine, N-cyclohexyl-β-alanine, N-cyclohexylmethyl-β-alanine, N-cyclohexyl-N-methyl-β-alanine, N-cyclohexylcarbonyl-β-alanine, N-(2'-pyridyl)-β-alanine, N-nicotinoyl-β-alanine, and β-alanine amide hydrochloride salt. On the other hand, many women on the panel were unable to continue with the irritation test due to strong sensory irritation caused by alanine which is disclosed as a conventional effective substance.

External compositions for skin are shown below as examples of preparations according to the present invention. Each of these compositions had an excellent effect, such as parakeratosis inhibition, pore shrinkage, rough skin preventing/ameliorating, or the like.

Preparation Example 1

Lotion

| Component | Amount added (mass %) |
|---|---|
| (1) 1,3-Butylene glycol | 6.0 |
| (2) Glycerin | 4.0 |
| (3) Oleyl alcohol | 0.1 |
| (4) POE (20) sorbitan monolaurate ester | 0.5 |
| (5) POE (15) lauryl alcohol ester | 0.5 |
| (6) Ethanol | 10.0 |
| (7) N-benzoyl-β-alanine | 1.0 |
| (8) Purified water | Balance |

(Preparation Method)

(1) and (2) were dissolved in purified water (8) at room temperature to thereby obtain an aqueous phase. The other components were dissolved in ethanol (6) and mixed with the aqueous phase to thereby solubilize. Then, N-benzoyl-β-alanine (7) was added. The product was filtered and packaged to obtain a lotion.

Preparations 2 Through 18

Lotion

The lotions of the Preparation Examples 2 through 18 were prepared similarly to the Preparation Example 1 by mixing the following amounts of components in place of the 1.0 mass % of N-benzoyl-β-alanine used in the components of Preparation Example 1. The amount of purified water added was adjusted so that the total amount of components added was brought to 100 mass % in each of the Preparation Examples: 1.0 mass % of N-(4'-methoxybenzoyl)-β-alanine (Preparation Example 2), 3.0 mass % of N-(3'-methoxybenzoyl)-β-alanine (Preparation Example 3), 3.0 mass % of N-(2'-methoxybenzoyl)-β-alanine (Preparation Example 4), 3.0 mass % of 3-(1'-piperidine)-propionic acid (Preparation Example 5), 3.0 mass % of N-benzyl-β-alanine (Preparation Example 6), 3.0 mass % of N-benzenesulfonyl-β-alanine (Preparation Example 7), 3.0 mass % of N-cyclohexyl-β-alanine (Preparation Example 8), 3.0 mass % of N-cyclohexylmethyl-3-alanine (Preparation Example 9), 3.0 mass % of N-cyclohexyl-N-methyl-β-alanine (Preparation Example 10), 1.0 mass % of N-(2'-pyridyl)-β-alanine (Preparation Example 11), 3.0 mass % of N-nicotinoyl-β-alanine (Preparation Example 12), 3.0 mass % of N-benzyloxycarbonyl-β-alanine (Preparation Example 13), 3.0 mass % of β-alanine amide hydrochloride salt (Preparation Example 14), 3.0 mass % of N-3',4',5'-trimethoxybenzoyl-β-alanine (Preparation Example 15), 3.0 mass % of N-phenylacetyl-β-alanine (Preparation Example 16), 3.0 mass % of N-cyclohexylcarbonyl-β-alanine (Preparation Example 17), and 0.5 mass % of N-benzoyl-β-alanine, 0.5 mass % of N-cyclohexyl-β-alanine, and 0.5 mass % of 3-(1'-piperidine)propionate (Preparation Example 18).

Preparation Example 19

Face Lotion

| Component | Amount added (mass %) |
| --- | --- |
| (Alcohol phase) | |
| (1) Ethanol | 10.0 |
| (2) Oleyl alcohol | 0.1 |
| (3) POE (20) sorbitan monolaurate ester | 0.5 |
| (4) POE (15) lauryl ether | 0.5 |
| (5) Preservative | As needed |
| (6) Fragrance | As needed |
| (Aqueous phase) | |
| (7) N-benzoyl-β-alanine | 1.0 |
| (8) 1,3-butyleneglycol | 6.0 |
| (9) Glycerin | 4.0 |
| (10) Deionized water | Balance |

(Preparation Method)
The aqueous phase and alcohol phase were each prepared and then these phases were mixed.

Preparation Examples 20 Through 35

Lotion

The lotions of Preparation Examples 20 through 35 were prepared similarly to the Preparation Example 19 by mixing the following amounts of components in place of the 1.0 mass % of N-benzoyl-β-alanine of the components of Preparation Example 19. The amount of deionized water added was adjusted so that the total amount of components added was brought to 100 mass % in each of the Preparation Examples: 1.0 mass % of N-(4'-methoxybenzoyl)-β-alanine (Preparation Example 20), 3.0 mass % of N-(3'-methoxybenzoyl)-β-alanine (Preparation Example 21), 3.0 mass % of N-(2'-methoxybenzoyl)-β-alanine (Preparation Example 22), 3.0 mass % of 3-(1'-piperidine)-propionic acid (Preparation Example 23), 3.0 mass % of N-benzyl-β-alanine (Preparation Example 24), 3.0 mass % of N-benzenesulfonyl-alanine (Preparation Example 25), 3.0 mass % of N-cyclohexyl-β-alanine (Preparation Example 26), 3.0 mass % of N-cyclohexylmethyl-β-alanine (Preparation Example 27), 3.0 mass % of N-cyclohexyl-N-methyl-β-alanine (Preparation Example 28), 1.0 mass % of N-(2'-pyridyl)-β-alanine (Preparation Example 29), 3.0 mass % of N-nicotinoyl-β-alanine (Preparation Example 30), 3.0 mass % of N-benzyloxycarbonyl-β-alanine (Preparation Example 31), 3.0 mass % of β-alanine amide hydrochloride salt (Preparation Example 32), 3.0 mass % of N-3',4',5'-trimethoxybenzoyl-β-alanine (Preparation Example 33), 3.0 mass % of N-phenylacetyl-β-alanine (Preparation Example 34), 3.0 mass % of N-cyclohexylcarbonyl-β-alanine (Preparation Example 35).

Preparation Example 36

Cream

| Component | Amount added (mass %) |
| --- | --- |
| (1) Stearyl alcohol | 6.0 |
| (2) Stearic acid | 2.0 |
| (3) Hydrogenated lanolin | 4.0 |
| (4) Squalene | 9.0 |
| (5) Octyl dodecanol | 10.0 |
| (6) 1,3-Butylene glycol | 6.0 |
| (7) PEG1500 | 4.0 |
| (8) POE(25)cetyl alcohol ester | 3.0 |
| (9) Glycerin monostearate | 2.0 |
| (10) N-benzoyl-β-alanine | 1.0 |
| (11) Tocopherol | 0.1 |
| (12) Purified water | Balance |

(Preparation Method)
(6) and (7) were added to purified water (12) and heated to 70° C. After (1) through (5) were heated and dissolved; (8), (9), and (11) were added thereto and the mixture was brought to 70° C. (10) was then added. This mixture was added to the aqueous phase, the emulsified particles were homogenized with a homomixer, and the product was degassed, filtered, and cooled to thereby obtain a cream.

Preparation Examples 37 Through 52

Cream

The cream of Preparation Examples 37 through 52 was prepared similarly to the Preparation Example 36 by mixing the following amounts of components in place of the 1.0 wt % of N-benzoyl-β-alanine of the components of the Preparation Example 36. The amount of purified water added was adjusted so that the total amount of components added was brought to 100 mass % in each of the Preparation Examples: 1.0 mass % of N-(4'-methoxybenzoyl)-alanine (Preparation Example 37), 3.0 mass % of N-(3'-methoxybenzoyl)-β-alanine (Preparation Example 38), 3.0 mass % of N-(2'-methoxybenzoyl)-β-alanine (Preparation Example 39), 3.0 mass % of 3-(1'-piperidine)-propionic acid (Preparation Example 40), 3.0 mass % of N-benzyl-β-alanine (Preparation Example 41), 3.0 mass % of N-benzenesulfonyl-β-alanine (Preparation Example 42), 3.0 mass % of N-cyclohexyl-β-alanine (Preparation Example 43), 3.0 mass % of N-cyclohexylmethyl-β-alanine (Preparation Example 44), 3.0 mass % of N-cyclohexyl-N-methyl-β-alanine (Preparation Example 45), 1.0 mass % of N-(2'-pyridyl)-β-alanine (Preparation Example 46), 3.0 mass % of N-nicotinoyl-β-alanine (Preparation Example 47), 3.0 mass % of N-benzyloxycarbonyl-β-alanine (Preparation Example 48), 3.0 mass % of β-alanine amide hydrochloride salt (Preparation Example 49), 3.0 mass % of N-3',4',5'-trimethoxybenzoyl-β-alanine (Preparation Example 50), 3.0 mass % of N-phenylacetyl-β-alanine (Preparation Example 51), and 3.0 mass % of N-cyclohexylcarbonyl-β-alanine (Preparation Example 52).

Preparation Example 53

Cream

| Component | Amount added (mass %) |
| --- | --- |
| (1) Stearic acid | 5.0 |
| (2) Stearyl alcohol | 4.0 |
| (3) Isopropyl myristate | 18.0 |
| (4) Glycerin monostearate ester | 3.0 |
| (5) Propylene glycol | 10.0 |
| (6) N-benzoyl-β-alanine | 2.0 |
| (7) Potassium hydroxide | 0.2 |
| (8) Sodium bisulfite | 0.01 |
| (9) Preservative | As needed |
| (10) Fragrance | As needed |
| (11) Deionized water | Balance |

(Preparation Method)
Propylene glycol, N-benzoyl-β-alanine, and potassium hydroxide were added to deionized water and dissolved, and then heated, and maintained at 70° C. (aqueous phase). The other components were mixed, then heated and melted, and maintained at 70° C. (oil phase) The oil phase was gradually added to the aqueous phase and pre-emulsified, then uniformly emulsified with a homomixer, and cooled to 30° C. while being thoroughly stirred.

Preparation Examples 54 Through 69

Cream

The cream of Preparation Examples 54 through 69 was prepared similarly to the Preparation Example 53 by mixing the following amounts of components added in place of the 2.0 mass % of N-benzoyl-β-alanine in the components of Preparation Example 53. The amount of ion-exchanged water added was adjusted so that the total amount of components added was brought to 100 mass % in each of the preparation examples: 2.0 mass % of N-(4'-methoxybenzoyl)-β-alanine (Preparation Example 54), 3.0 mass % of N-(3'-methoxybenzoyl)-β-alanine (Preparation Example 55), 3.0 mass % of N-(2'-methoxybenzoyl)-β-alanine (Preparation Example 56), 3.0 mass % of 3-(1'-piperidine)-propionic acid (Preparation Example 57), 3.0 mass % of N-benzyl-β-alanine (Preparation Example 58), 3.0 mass % of N-benzenesulfonyl-β-alanine (Preparation Example 59), 3.0 mass % of N-cyclohexyl-β-alanine (Preparation Example 60), 3.0 mass % of N-cyclohexylmethyl-β-alanine (Preparation Example 61), 3.0 mass % of N-cyclohexyl-N-methyl-β-alanine (Preparation Example 62), 1.0 mass % of N-(2'-pyridyl)-β-alanine (Preparation Example 63), 3.0 mass % of N-nicotinoyl-β-alanine (Preparation Example 64), 3.0 mass % of N-benzyloxycarbonyl-β-alanine (Preparation Example 65), 3.0 mass % of β-alanine amide hydrochloride salt (Preparation Example 66), 3.0 mass % of N-3',4',5'-trimethoxybenzoyl-β-alanine (Preparation Example 67), 3.0 mass % of N-phenylacetyl-jβ-alanine (Preparation Example 68), and 3.0 mass % of N-cyclohexylcarbonyl-β-alanine (Preparation Example 69).

Preparation Example 70

Clarifying Lotion

| Component | Amount added (mass %) |
| --- | --- |
| (Phase A) | |
| (1) Ethyl alcohol (95%) | 10.0 |
| (2) POE (20) octyl dodecanol | 1.0 |
| (3) Pantothenyl ethyl ether | 0.1 |
| (4) ASDA•4Na | 1.5 |
| (5) Methyl paraben | 0.15 |
| (6) Ethanol | 10.0 |
| (Phase B) | |
| (7) Potassium hydroxide | 0.1 |
| (Phase C) | |
| (8) Glycerin | 5.0 |
| (9) Dipropylene glycol | 10.0 |
| (10) N-benzoyl-β-alanine | 2.0 |
| (11) Carboxyvinyl polymer | 0.2 |
| (12) Purified water | Balance |

(Preparation Method)
Phases A and C were each uniformly dissolved, and phase A was added to phase C solubilize. Then phase B was added and mixed.

Preparation Examples 71 Through 86

Clarifying Lotion

The clarifying lotion of Preparation Examples 71 through 86 was prepared similarly to the Preparation Example 70 by mixing the following amounts of components added in place of the 2.0 mass % of N-benzoyl-β-alanine of the components of Preparation Example 70. The amount of purified water added was adjusted so that the total amount of components added was brought to 100 mass % in each of the preparation examples: 2.0 mass % of N-(4'-methoxybenzoyl)-β-alanine (Preparation Example 71), 3.0 mass % of N-(3'-methoxybenzoyl)-β-alanine (Preparation Example 72), 3.0 mass % of N-(2'-methoxybenzoyl)-β-alanine (Preparation Example 73), 3.0 mass % of 3-(1'-piperidine)-propionic acid (Preparation Example 74), 3.0 mass % of N-benzyl-Jβ-alanine (Preparation Example 75), 3.0 mass % of N-benzenesulfonyl-β-alanine (Preparation Example 76), 3.0 mass % of N-cyclohexyl-β-alanine (Preparation Example 77), 3.0 mass % of N-cyclohexylmethyl-β-alanine (Preparation Example 78), 3.0 mass % of N-cyclohexyl-N-methyl-β-alanine (Preparation Example 79), 1.0 mass % of N-(2'-pyridyl)-β-alanine (Preparation Example 80), 3.0 mass % of N-nicotinoyl-β-alanine (Preparation Example 81), 3.0 mass % of N-benzyloxycarbonyl-β-alanine (Preparation Example 82), 3.0 mass % of β-alanine amide hydrochloride salt (Preparation Example 83), 3.0 mass % of N-3',4',5'-trimethoxybenzoyl-β-alanine (Preparation Example 84), 3.0 mass % of N-phenylacetyl-β-alanine (Preparation Example 85), and 3.0 mass % of N-cyclohexylcarbonyl-β-alanine (Preparation Example 86).

Preparation Example 87

Milky Lotion

| Component | Amount added (mass %) |
| --- | --- |
| (1) Stearic acid | 2.5 |
| (2) Cetyl alcohol | 1.5 |
| (3) Vaseline | 5.0 |
| (4) Liquid paraffin | 10.0 |
| (5) POE (10) monooleate ester | 2.0 |
| (6) PEG 1500 | 3.0 |
| (7) Triethanolamine | 1.0 |
| (8) N-benzoyl-β-alanine | 0.5 |
| (9) Sodium bisulfite | 0.01 |
| (10) Ethyl paraben | 0.3 |
| (11) Carboxyvinyl polymer | 0.05 |
| (12) Fragrance | As needed |
| (13) Deionized water | Balance |

(Preparation Method)

Carboxyvinyl polymer was dissolved in a small amount of deionized water (phase A). PEG 1500, N-benzoyl-β-alanine, and triethanol amine were added to the balance of the deionized water, and it was heated and dissolved, and maintained at 70° C. (aqueous phase). The other components were mixed, heated, melted, and maintained at 70° C. (oil phase). The oil phase was added to the aqueous phase and pre-emulsified, phase A was added and uniformly emulsified with a homomixer, and the product was cooled to 30° C. while being thoroughly agitated.

Preparation Examples 88 Through 103

Milky Lotion

The milky lotion of Preparation Examples 88 through 103 was prepared similarly to Preparation Example 87 by mixing the following amounts of components added in place of the 0.5 mass % of N-benzoyl-β-alanine of the components of Preparation Example 87. The amount of deionized water added was adjusted so that the total amount of components added was brought to 100 mass % in each of the preparation examples: 0.5 mass % of N-(4'-methoxybenzoyl)-β-alanine (Preparation Example 88), 0.5 mass % of N-(3'-methoxybenzoyl)-β-alanine (Preparation Example 89), 1.0 mass % of N-(2'-methoxybenzoyl)-β-alanine (Preparation Example 90), 1.0 mass % of 3-(1'-piperidine)-propionic acid (Preparation Example 91), 1.0 mass % of N-benzyl-β-alanine (Preparation Example 92), 3.0 mass % of N-benzenesulfonyl-β-alanine (Preparation Example 93), 1.0 mass % of N-cyclohexyl-β-alanine (Preparation Example 94), 1.0 mass % of N-cyclohexylmethyl-β-alanine (Preparation Example 95), 3.0 mass % of N-cyclohexyl-N-methyl-β-alanine (Preparation Example 96), 1.0 mass % of N-(2'-pyridyl)-β-alanine (Preparation Example 97), 1.0 mass % of N-nicotinoyl-β-alanine (Preparation Example 98), 1.0 mass % of N-benzyloxycarbonyl-β-alanine (Preparation Example 99), 1.0 mass % of β-alanine amide hydrochloride salt (Preparation Example 100), 1.0 mass % of N-3',4',5'-trimethoxybenzoyl-β-alanine (Preparation Example 101), 1.0 mass % of N-phenylacetyl-β-alanine (Preparation Example 102), and 1.0 mass % of N-cyclohexylcarbonyl-β-alanine (Preparation Example 103).

Preparation Example 104

Gel

| Component | Amount added (mass %) |
| --- | --- |
| (1) 95% Ethanol | 10.0 |
| (2) Dipropylene glycol | 15.0 |
| (3) POE (15) oleyl alcohol ether | 2.0 |
| (4) N-benzoyl-β-serine | 1.0 |
| (5) Sodium bisulfite | 0.03 |
| (6) Carboxyvinyl polymer ("Carbopol 941") | 1.0 |
| (7) Potassium hydroxide | 0.15 |
| (8) L-arginine | 0.1 |
| (9) Fragrance | As needed |
| (10) Preservative | As needed |
| (11) Purified water | Balance |

(Preparation Method)

(4) and (6) were uniformly dissolved in purified water (11) (aqueous phase). On the other hand, (2), (3), (5), (9), and (10) were dissolved in (1), and the product was added to the aqueous phase. The mixture was neutralized and thickened by (7) and (8) to obtain a gel.

Preparation Examples 105 Through 120

Gel

The gel of Preparation Examples 105 through 120 was prepared similarly to Preparation Example 104 by mixing the following amounts of components added in place of the 1.0 mass % of N-benzoyl-β-alanine of the components of Preparation Example 104. The amount of purified water added was adjusted so that the total amount of components added was brought to 100 mass % in each of the Preparation Examples: 1.0 mass % of N-(4'-methoxybenzoyl)-β-alanine (Preparation Example 105), 1.0 mass % of N-(3'-methoxybenzoyl)-β-alanine (Preparation Example 106), 3.0 mass % of N-(2'-methoxybenzoyl)-β-alanine (Preparation Example 107), 3.0 mass % of 3-(1'-piperidine)-propionic acid (Preparation Example 108), 3.0 mass % of N-benzyl-β-alanine (Preparation Example 109), 3.0 mass % of N-benzenesulfonyl-β-alanine (Preparation Example 110), 3.0 mass % of N-cyclohexyl-β-alanine (Preparation Example 111), 3.0 mass % of N-cyclohexylmethyl-β-alanine (Preparation Example 112), 3.0 mass % of N-cyclohexyl-N-methyl-β-alanine (Preparation Example 113), 1.0 mass % of N-(2'-pyridyl)-β-alanine (Preparation Example 114), 3.0 mass % of N-nicotinoyl-β-alanine (Preparation Example 115), 3.0 mass % of N-benzyloxycarbonyl-β-alanine (Preparation Example 116), 3.0 mass % of β-alanine amide hydrochloride salt (Preparation Example 117), 3.0 mass % of N-3',4',5'-trimethoxybenzoyl-β-alanine (Preparation Example 1118), 3.0 mass % of N-phenylacetyl-β-alanine (Preparation Example 119), and 3.0 mass % of N-cyclohexylcarbonyl-β-alanine (Preparation Example 120).

Preparation Example 121

Pack

| Component | Amount added (mass %) |
| --- | --- |
| (Phase A) | |
| Dipropylene glycol | 5.0 |
| POE(60)hydrogenated castor oil | 5.0 |
| (Phase B) | |
| Olive oil | 5.0 |
| Tocopherol acetate | 0.2 |
| Ethyl paraben | 0.2 |
| Fragrance | 0.2 |
| (Phase C) | |
| N-benzoyl-β-alanine | 1.0 |
| Sodium bisulfite | 0.03 |
| Polyvinyl alcohol (degree of saponification of 90, degree of polymerization of 2,000) | 13.0 |
| Ethanol | 7.0 |
| Deionized water | Balance |

(Preparation Method)

Phases A, B, and C were uniformly dissolved, and phase B was added to phase A to solubilize microemulsion. Next, the microemulsion was added to phase C and mixed.

Preparation Examples 122 Through 137

Pack

The pack of Preparation Examples 122 through 137 was prepared similarly to Preparation Example 121 by mixing the following amounts of components added in place of the 1.0 mass % of N-benzoyl-β-alanine of the components of Preparation Example 121. The amount of deionized water added was adjusted so that the total amount of components added was brought to 100 mass % in each of the Preparation Examples: 1.0 mass % of N-(4'-methoxybenzoyl)-β-alanine (Preparation Example 122), 1.0 mass % of N-(3'-methoxybenzoyl)-β-alanine (Preparation Example 123), 3.0 mass % of N-(2'-methoxybenzoyl)-β-alanine (Preparation Example 124), 3.0 mass % of 3-(1'-piperidine)-propionic acid (Preparation Example 125), 3.0 mass % of N-benzyl-β-alanine (Preparation Example 126), 3.0 mass % of N-benzenesulfonyl-β-alanine (Preparation Example 127), 3.0 mass % of N-cyclohexyl-β-alanine (Preparation Example 128), 3.0 mass % of N-cyclohexylmethyl-β-alanine (Preparation Example 129), 3.0 mass % of N-cyclohexyl-N-methyl-β-alanine (Preparation Example 130), 1.0 mass % of N-(2'-pyridyl)-β-alanine (Preparation Example 131), 3.0 mass % of N-nicotinoyl-β-alanine (Preparation Example 132), 3.0 mass % of N-benzyloxycarbonyl-β-alanine (Preparation Example 133), 3.0 mass % of β-alanine amide hydrochloride salt (Preparation Example 134), 3.0 mass % of N-3',4',5'-trimethoxybenzoyl-β-alanine (Preparation Example 135), 3.0 mass % of N-phenylacetyl-β-alanine (Preparation Example 136), and 3.0 mass % of N-cyclohexylcarbonyl-β-alanine (Preparation Example 137).

Preparation Example 138

Peel-Off Pack

| Component | Amount added (mass %) |
| --- | --- |
| (Alcohol phase) | |
| 95% Ethanol | 10.0 |
| POE(15) Oleyl alcohol ether | 2.0 |
| Preservative | As needed |
| Fragrance | As needed |
| (Aqueous phase) | |
| N-benzoyl-β-alanine | 3.0 |
| Glutathione | 3.0 |
| Arbutin | 3.0 |
| Polyvinyl alcohol | 12.0 |
| PEG1500 | 1.0 |
| Deionized water | Balance |

(Preparation Method)

The aqueous phase was prepared at 80° C. and then cooled to 50° C. The alcohol phase prepared at room temperature was subsequently added and then uniformly mixed and set aside to cool.

Preparation Examples 139 Through 154

Peel-Off Pack

The peel-off pack of Preparation Examples 139 through 154 was prepared similarly to Preparation Example 138 by mixing the following amounts of components added in place of the 3.0 mass % of N-benzoyl-β-alanine of the components of Preparation Example 138. The amount of deionized water added was adjusted so that the total amount of components added was brought to 100 mass % in each of the Preparation Examples: 2.0 mass % of N-(4'-methoxybenzoyl)-β-alanine (Preparation Example 139), 3.0 mass % of N-(3'-methoxybenzoyl)-β-alanine (Preparation Example 140), 3.0 mass % of N-(2'-methoxybenzoyl)-β-alanine (Preparation Example 141), 3.0 mass % of 3-(1'-piperidine)-propionic acid (Preparation Example 142), 3.0 mass % of N-benzyl-β-alanine (Preparation Example 143), 3.0 mass % of N-benzenesulfonyl-β-alanine (Preparation Example 144), 3.0 mass % of N-cyclohexyl-β-alanine (Preparation Example 145), 3.0 mass % of N-cyclohexylmethyl-β-alanine (Preparation Example 146), 3.0 mass % of N-cyclohexyl-N-methyl-β-alanine (Preparation Example 147), 1.0 mass % of N-(2'-pyridyl)-3-alanine (Preparation Example 148), 3.0 mass % of N-nicotinoyl-β-alanine (Preparation Example 149), 3.0 mass % of N-benzyloxycarbonyl-β-alanine (Preparation Example 150), 3.0 mass % of β-alanine amide hydrochloride salt (Preparation Example 151), 3.0 mass % of N-3',4',5'-trimethoxybenzoyl-β-alanine (Preparation Example 152), 3.0 mass % of N-phenylacetyl-β-alanine (Preparation Example 153), and 3.0 mass % of N-cyclohexylcarbonyl-β-alanine (Preparation Example 154).

Preparation Example 155

Powdered Pack

| Components | Amount added (mass %) |
|---|---|
| (Alcohol phase) | |
| 95% Ethanol | 2.0 |
| Preservative | As needed |
| Fragrance | As needed |
| Pigment | As needed |
| (Aqueous phase) | |
| N-benzoyl-β-alanine | 3.0 |
| Propylene glycol | 7.0 |
| Zinc oxide | 25.0 |
| Kaolin | 20.0 |
| Deionized water | Balance |

(Preparation Method)

The aqueous phase was uniformly prepared at room temperature. Then the alcohol phase prepared at room temperature was added and uniformly mixed.

Preparation Examples 156 Through 171

Powdered Pack

The powdered pack of Preparation Examples 156 through 171 was prepared similarly to Preparation Example 155 by mixing the following amounts of components added in place of the 3.0 mass % of N-benzoyl-β-alanine of the components of Preparation Example 155. The amount of deionized water added was adjusted so that the total amount of components added was brought to 100 mass % in each of the Preparation Examples: 3.0 mass % of N-(4'-methoxybenzoyl)-β-alanine (Preparation Example 156), 3.0 mass % of N-(3'-methoxybenzoyl)-β-alanine (Preparation Example 157), 3.0 mass % of N-(2'-methoxybenzoyl)-β-alanine (Preparation Example 158), 3.0 mass % of 3-(1'-piperidine)-propionic acid (Preparation Example 159), 3.0 mass % of N-benzyl-jβ-alanine (Preparation Example 160), 3.0 mass % of N-benzenesulfonyl-β-alanine (Preparation Example 161), 3.0 mass % of N-cyclohexyl-β-alanine (Preparation Example 162), 3.0 mass % of N-cyclohexylmethyl-β-alanine (Preparation Example 163), 3.0 mass % of N-cyclohexyl-N-methyl-β-alanine (Preparation Example 164), 1.0 mass % of N-(2'-pyridyl)-β-alanine (Preparation Example 165), 3.0 mass % of N-nicotinoyl-β-alanine (Preparation Example 166), 3.0 mass % of N-benzyloxycarbonyl-β-alanine (Preparation Example 167), 3.0 mass % of β-alanine amide hydrochloride salt (Preparation Example 168), 3.0 mass % of N-3',4',5'-trimethoxybenzoyl-β-alanine (Preparation Example 169), 3.0 mass % of N-phenylacetyl-β-alanine (Preparation Example 170), and 3.0 mass % of N-cyclohexylcarbonyl-β-alanine (Preparation Example 171).

Preparation Example 172

Solid Powder Foundation

| Component | Amount added (mass %) |
|---|---|
| (1) Talc | 15.0 |
| (2) Sericite | 10.0 |
| (3) Spherical nylon powder | 10.0 |
| (4) Porous silicic anhydride powder | 15.0 |
| (5) Boron nitride | 5.0 |
| (6) Titanium dioxide | 5.0 |
| (7) Iron oxide | 3.0 |
| (8) Zinc stearate | 5.0 |
| (9) N-benzoyl-β-alanine | 3.0 |
| (10) Liquid paraffin | Balance |
| (11) Glycerin triisooctanoate | 15.0 |
| (12) Sorbitan sesquioleate | 1.5 |
| (13) Preservative | As needed |
| (14) Fragrance | As needed |

(Preparation Method)

A mixture of components (9) through (14) was added, stirred, and mixed as components (1) through (8) were being mixed and ground. The mixture was molded into a pot to obtain a solid powder foundation.

Preparation Examples 173 Through 187

Solid Powder Foundation

The solid powder foundation of Preparation Examples 173 through 187 was prepared similarly to Preparation Example 172 by mixing the following amounts of components added in place of the 3.0 mass % of N-benzoyl-β-alanine of the components of Preparation Example 172. The amount of liquid paraffin added was adjusted so that the total amount of components added was brought to 100 mass % in each of the Preparation Examples: 3.0 mass % of N-(4'-methoxybenzoyl)-β-alanine (Preparation Example 173), 3.0 mass % of N-(3'-methoxybenzoyl)-β-alanine (Preparation Example 174), 3.0 mass % of N-(2'-methoxybenzoyl)-β-alanine (Preparation Example 175), 3.0 mass % of 3-(1'-piperidine)-propionic acid (Preparation Example 176), 3.0 mass % of N-benzyl-β-alanine (Preparation Example 177), 3.0 mass % of N-benzenesulfonyl-β-alanine (Preparation Example 178), 3.0 mass % of N-cyclohexyl-β-alanine (Preparation Example 179), 3.0 mass % of N-cyclohexylmethyl-β-alanine (Preparation Example 180), 3.0 mass % of N-cyclohexyl-N-methyl-β-alanine (Preparation Example 181), 1.0 mass % of N-(2'-pyridyl)-β-alanine (Preparation Example 182), 3.0 mass % of N-nicotinoyl-β-alanine (Preparation Example 183), 3.0 mass % of N-benzyloxycarbonyl-β-alanine (Preparation Example 184), 3.0 mass % of β-alanine amide hydrochloride salt (Preparation Example 185), 3.0 mass % of N-3',4',5'-trimethoxybenzoyl-β-alanine (Preparation Example 186), 3.0 mass % of N-phenylacetyl-β-alanine (Preparation Example 187), and 3.0 mass % of N-cyclohexylcarbonyl-β-alanine (Preparation Example 188).

Preparation Example 189

Water-in-Oil Emulsified Foundation

| Component | Amount added (mass %) |
|---|---|
| (1) Spherical nylon | 10.0 |
| (2) Porous silicic anhydride powder | 8.0 |
| (3) Mica titanium | 2.0 |
| (4) Silicone-treated sericite | 2.0 |
| (5) Silicone-treated mica | 12.0 |
| (6) Silicone-treated titanium dioxide | 5.0 |
| (7) Silicone-treated iron oxide | 2.0 |
| (8) Deionized water | Balance |
| (9) N-benzoyl-β-alanine | 3.0 |
| (10) Decamethylcyclopentane siloxane | 18.0 |
| (11) Dimethyl polysiloxane | 5.0 |
| (12) Squalene | 1.0 |
| (13) POE-modified dimethyl polysiloxane | 2.0 |
| (14) Preservative | As needed |
| (15) Fragrance | As needed |

(Preparation Method)

Mixed and ground (1) through (7) were added and dispersed in a uniformly mixed solution of components (9) through (15). (8) was added to this dispersion, emulsified, and filled into a container to obtain a water-in-oil emulsified foundation.

Preparation Examples 190 Through 205

Water-in-Oil Emulsified Foundation

The water-in-oil emulsified foundation of Preparation Examples 190 through 205 was prepared similarly to Preparation Example 189 by mixing the following amounts of components added in place of the 3.0 mass % of N-benzoyl-β-alanine of the components of Preparation Example 189. The amount of deionized water added was adjusted so that the total amount of components added was brought to 100 mass % in each of the Preparation Examples: 3.0 mass % of N-(4'-methoxybenzoyl)-β-alanine (Preparation Example 190), 3.0 mass % of N-(3'-methoxybenzoyl)-β-alanine (Preparation Example 191), 3.0 mass % of N-(2'-methoxybenzoyl)-β-alanine (Preparation Example 192), 3.0 mass % of 3-(1'-piperidine)-propionic acid (Preparation Example 193), 3.0 mass % of N-benzyl-β-alanine (Preparation Example 194), 3.0 mass % of N-benzenesulfonyl-β-alanine (Preparation Example 195), 3.0 mass % of N-cyclohexyl-β-alanine (Preparation Example 196), 3.0 mass % of N-cyclohexylmethyl-β-alanine (Preparation Example 197), 3.0 mass % of N-cyclohexyl-N-methyl-β-alanine (Preparation Example 198), 1.0 mass % of N-(2'-pyridyl)-β-alanine (Preparation Example 199), 3.0 mass % of N-nicotinoyl-β-alanine (Preparation Example 200), 3.0 mass % of N-benzyloxycarbonyl-β-alanine (Preparation Example 201), 3.0 mass % of β-alanine amide hydrochloride salt (Preparation Example 202), 3.0 mass % of N-3',4',5'-trimethoxybenzoyl-β-alanine (Preparation Example 203), 3.0 mass % of N-phenylacetyl-β-alanine (Preparation Example 204), and 3.0 mass % of N-cyclohexylcarbonyl-β-alanine (Preparation Example 205).

INDUSTRIAL APPLICABILITY

The β-alanine derivatives represented by general formula (1), (2), or (3) according to the present invention and salts thereof have the excellent function of inhibiting parakeratosis, shrinking pores, and preventing/ameliorating rough skin; therefore, and are used in cosmetics including non-medical products, pharmaceutical products, food products, and various other fields as parakeratosis inhibitors, pore-shrinking agents, and rough skin preventing/ameliorating agents. Moreover, the β-alanine derivatives represented by the general formula (1), (2), or (3) and salts thereof are added, in particular, to an external composition for skin and used in cosmetic products including non-medical products, in pharmaceutical products, and in other fields as an external composition for skin having a function such as parakeratosis inhibition, pore shrinkage, or rough skin prevention/abatement.

The invention claimed is:

1. A method of inhibiting parakeratosis by applying to skin a composition comprising one or more p-alanine derivatives selected from the group consisting of:
   3-(1'-piperidine)-propionic acid,
   N-monomethyl-β-alanine,
   N-cyclohexyl-β-alanine,
   N-cyclohexylmethyl-β-alanine,
   N-cyclohexyl-N-methyl-β-alanine,
   N-cyclohexylcarbonyl-β-alanine,
   N-(2'-pyridyl)-β-alanine,
   N-benzyl-β-alanine,
   N-β-anisoyl-β-alanine (N-4'-methoxybenzoyl-β-alanine),
   N-m-anisoyl-β-alanine (N-3'-methoxybenzoyl-β-alanine),
   N-o-anisoyl-β-alanine (N-2'-methoxybenzoyl-β-alanine),
   N-3',4',5'-trimethoxybenzoyl-β-alanine, and
   N-phenylacetyl-β-alanine, as well as a salt thereof.

2. The method of inhibiting parakeratosis according to claim 1, wherein the β-alanine derivative is 3-(1'-piperidine)-propionic acid or a salt thereof.

3. A method for shrinking pores by applying to skin a composition comprising one or more p-alanine derivatives selected from the group consisting of:
   3-(1'-piperidine)-propionic acid,
   N-monomethyl-β-alanine,
   N-cyclohexyl-β-alanine,
   N-cyclohexylmethyl-β-alanine,
   N-cyclohexyl-N-methyl-β-alanine,
   N-cyclohexylcarbonyl-β-alanine,
   N-(2'-pyridyl)-β-alanine,
   N-benzyl-β-alanine,
   N-β-anisoyl-β-alanine (N-4'-methoxybenzoyl-β-alanine),
   N-m-anisoyl-β-alanine (N-3'-methoxybenzoyl-β-alanine),
   N-o-anisoyl-β-alanine (N-2'-methoxybenzoyl-β-alanine),
   N-3',4',5'-trimethoxybenzoyl-β-alanine, and
   N-phenylacetyl-β-alanine, as well as salts thereof.

4. The method for shrinking pores according to claim 3, wherein the β-alanine derivative is 3-(1'-piperidine)-propionic acid or a salt thereof.

5. A method of rough skin prevention/ameliorating by applying to skin a composition comprising one or more β-alanine derivatives selected from the group consisting of:
   3-(1'-piperidine)-propionic acid,
   N-monomethyl-β-alanine,
   N-cyclohexyl-β-alanine,
   N-cyclohexylmethyl-β-alanine,
   N-cyclohexyl-N-methyl-β-alanine,
   N-cyclohexylcarbonyl-β-alanine,
   N-(2'-pyridyl)-β-alanine,
   N-benzyl-β-alanine,
   N-p-anisoyl-β-alanine (N-4'-methoxybenzoyl-β-alanine), N-m-anisoyl-β-alanine (N-3'-methoxybenzoyl-β-alanine),
N-o-anisoyl-β-alanine (N-2'-methoxybenzoyl-β-alanine),
N-3',4',5'-trimethoxybenzoyl-β-alanine, and
N-phenylacetyl-β-alanine, as well as salts thereof.

6. The method of rough skin prevention/ameliorating according to claim 5, wherein the β-alanine derivative is 3-(1'-piperidine)-propionic acid or a salt thereof.

7. An external composition for skin, containing 3-(1'-piperidine)-propionic acid and pharmaceutically acceptable carrier.

* * * * *